US012678552B2

(12) United States Patent
Adams et al.

(10) Patent No.: US 12,678,552 B2
(45) Date of Patent: Jul. 14, 2026

(54) SYSTEMS AND METHODS FOR CONTROLLING DUAL MODE NEGATIVE PRESSURE WOUND THERAPY APPARATUS

(71) Applicant: Smith & Nephew Asia Pacific Pte. Limited, Singapore (SG)

(72) Inventors: Eric Edward Adams, Pittsboro, NC (US); Ben Alan Askem, Leeds (GB); Kevin Bendele, Fort Worth, TX (US); Aaron Michael Husz, Cary, NC (US); David Edward Lee, Durham, NC (US); Nisha Mistry, Dubai (AE); Lee Michael Rush, St. Petersburg, FL (US); David Ronald Upton, New Hill, NC (US); Gareth Walker, Hull (GB); William Jacob Ward, Apex, NC (US); Hannah Bailey Sidebottom, Hull (GB)

(73) Assignee: Smith & Nephew Asia Pacific Pte. Limited, Singapore (SG)

( * ) Notice: Subject to any disclaimer, the term of this patent is extended or adjusted under 35 U.S.C. 154(b) by 689 days.

(21) Appl. No.: 18/099,844

(22) Filed: Jan. 20, 2023

(65) Prior Publication Data

US 2023/0293805 A1     Sep. 21, 2023

Related U.S. Application Data

(63) Continuation of application No. 17/043,519, filed as application No. PCT/IB2019/053508 on Apr. 29, 2019, now Pat. No. 11,559,619.
(Continued)

(51) Int. Cl.
    *A61M 1/00*          (2006.01)

(52) U.S. Cl.
    CPC .............. *A61M 1/915* (2021.05); *A61M 1/90* (2021.05); *A61M 1/73* (2021.05); *A61M 1/74* (2021.05); *A61M 2205/14* (2013.01)

(58) Field of Classification Search
    CPC ........... A61M 1/73; A61M 1/90; A61M 1/74; A61M 1/915; A61M 2205/14;
    (Continued)

(56) References Cited

U.S. PATENT DOCUMENTS

| D239,019 S | 3/1976 | Flinn |
| 4,328,828 A | 5/1982 | Cianci |
| (Continued) |

FOREIGN PATENT DOCUMENTS

| DE | 102015215165 A1 | 2/2017 |
| EP | 0883430 B1 | 1/2007 |
| (Continued) |

OTHER PUBLICATIONS

International Preliminary Report on Patentability and Written Opinion for Application No. PCT/IB2019/053508, mailed on Nov. 12, 2020, 9 pages.
(Continued)

*Primary Examiner* — Andrew J Mensh
(74) *Attorney, Agent, or Firm* — Knobbe, Martens, Olson & Bear, LLP

(57) ABSTRACT

In some embodiments, a negative pressure wound therapy device includes a negative pressure source and a controller configured to, in response to determining that the negative pressure source is directly fluidically connected to a wound dressing without a canister between the two, operate the negative pressure source in a first mode; otherwise, operate the negative pressure source in a second, different mode. The controller can be further configured to, in response to determining that a level of activity of the negative pressure
(Continued)

6400 ⟍     Leak Occurs and Fixed in Time, then Reoccur

Leak Alert Warning Raised at 10 Minutes into Leak
Leak Starts
Leak Fixed     Leak Occurs Again No Leak Alert     Leak Alert     No Leak Alert     Leak Alert Leak Counter = 1
Leak Counter = 10
6406
When Leak Reoccurs, Duty Cycle is above Threshold, Leak Counter is Incremented again

①②③④⑤⑥⑦⑧⑨⑩⑪⑫⑬     ⑦⑧⑨⑩⑪⑫⑬
6408

Leak (4 % Canisterless; 12% Canister)

6102
Leak (4% Canisterless; 12% Canister)

When Leak is Fixed, Leak Counter is Decrement from 10
⑨⑧⑦⑥⑤
6402  6404
2 Mins into Leak Fixed, leak Alert is cleared

⑩⑧

Block (0.5%)
6104
Block(0.5%)

Pump Duty Cycle (%)

Time (1 minute Resolution)

source over a first time duration satisfies at least one of a leak or blockage condition, provide an indication of at least one of a leak or blockage and, in response to determining that the level of activity does not satisfy the at least one of the leak or blockage condition over a second time duration subsequent to the first time duration, discontinue providing the indication.

19 Claims, 15 Drawing Sheets

Related U.S. Application Data

(60) Provisional application No. 62/664,688, filed on Apr. 30, 2018.

(58) Field of Classification Search
CPC .......... A61F 5/445; A61F 5/443; A61F 13/42;
A61F 13/00055; A61B 5/746
USPC ........................................................ 604/543
See application file for complete search history.

(56) References Cited

U.S. PATENT DOCUMENTS

| | | | |
|---|---|---|---|
| 4,498,850 A | 2/1985 | Perlov et al. | |
| 4,731,076 A | 3/1988 | Noon et al. | |
| D357,735 S | 4/1995 | McPhee | |
| 5,514,088 A | 5/1996 | Zakko | |
| 5,712,795 A | 1/1998 | Layman et al. | |
| 6,027,490 A | 2/2000 | Radford et al. | |
| 6,203,291 B1 | 3/2001 | Stemme et al. | |
| 6,232,680 B1 | 5/2001 | Bae et al. | |
| 6,396,407 B1 | 5/2002 | Kobayashi | |
| D475,132 S | 5/2003 | Randolph | |
| 7,004,915 B2 | 2/2006 | Boynton et al. | |
| 7,022,113 B2 | 4/2006 | Lockwood et al. | |
| 7,070,584 B2 | 7/2006 | Johnson et al. | |
| 7,214,202 B1 | 5/2007 | Vogel et al. | |
| D581,042 S | 11/2008 | Randolph et al. | |
| D590,934 S | 4/2009 | Randolph et al. | |
| D602,582 S | 10/2009 | Pidgeon et al. | |
| D602,583 S | 10/2009 | Pidgeon et al. | |
| D602,584 S | 10/2009 | Pidgeon et al. | |
| 7,608,066 B2 | 10/2009 | Vogel | |
| 7,611,500 B1 | 11/2009 | Lina et al. | |
| 7,857,806 B2 | 12/2010 | Karpowicz et al. | |
| 7,927,319 B2 | 4/2011 | Lawhorn | |
| 7,976,598 B2 | 7/2011 | Matula et al. | |
| D645,137 S | 9/2011 | Gonzalez | |
| 8,021,348 B2 | 9/2011 | Risk, Jr. et al. | |
| 8,062,272 B2 | 11/2011 | Weston | |
| 8,066,243 B2 | 11/2011 | Svedman et al. | |
| 8,070,735 B2 | 12/2011 | Koch et al. | |
| D654,164 S | 2/2012 | Cole et al. | |
| D660,409 S | 5/2012 | Taggerty et al. | |
| 8,215,929 B2 | 7/2012 | Shen et al. | |
| 8,216,197 B2 | 7/2012 | Simmons et al. | |
| 8,226,620 B2 | 7/2012 | Giezendanner et al. | |
| 8,308,714 B2 | 11/2012 | Weston et al. | |
| 8,317,774 B2 | 11/2012 | Adahan | |
| 8,366,692 B2 | 2/2013 | Weston et al. | |
| 8,409,160 B2 | 4/2013 | Locke et al. | |
| 8,480,641 B2 | 7/2013 | Jacobs | |
| 8,540,688 B2 | 9/2013 | Eckstein et al. | |
| 8,617,129 B2 * | 12/2013 | Hartwell .............. A61M 1/966 604/313 | |
| 8,641,693 B2 | 2/2014 | Locke et al. | |
| 8,668,677 B2 | 3/2014 | Eckstein et al. | |
| 8,827,967 B2 | 9/2014 | Lawhorn | |
| 8,858,517 B2 | 10/2014 | Pan et al. | |
| 8,905,985 B2 | 12/2014 | Allen et al. | |
| 9,050,398 B2 | 6/2015 | Armstrong et al. | |
| 9,084,845 B2 | 7/2015 | Adie et al. | |
| 9,138,531 B2 | 9/2015 | Yodfat et al. | |
| 9,199,010 B2 | 12/2015 | Yao et al. | |
| D750,222 S | 2/2016 | Chang | |
| D750,235 S | 2/2016 | Maurice | |
| D750,236 S | 2/2016 | Maurice | |
| D757,260 S | 5/2016 | Lombardi, III et al. | |
| 9,327,063 B2 | 5/2016 | Locke et al. | |
| 9,333,281 B2 | 5/2016 | Giezendanner et al. | |
| D764,047 S | 8/2016 | Bjelovuk et al. | |
| D764,048 S | 8/2016 | Bjelovuk et al. | |
| D764,653 S | 8/2016 | Bjelovuk et al. | |
| D764,654 S | 8/2016 | Bjelovuk et al. | |
| 9,415,199 B2 | 8/2016 | Tsai | |
| 9,427,505 B2 | 8/2016 | Askem et al. | |
| D765,830 S | 9/2016 | Bjelovuk et al. | |
| 9,445,948 B2 | 9/2016 | Smola | |
| D773,658 S | 12/2016 | Bow | |
| 9,586,036 B2 | 3/2017 | Masuda et al. | |
| 9,597,107 B2 | 3/2017 | Staid et al. | |
| D788,293 S | 5/2017 | Eckstein et al. | |
| D791,939 S | 7/2017 | Turturro et al. | |
| D792,586 S | 7/2017 | Becker | |
| 9,737,649 B2 | 8/2017 | Begin et al. | |
| D797,275 S | 9/2017 | Evans et al. | |
| D802,744 S | 11/2017 | Bjelovuk et al. | |
| 9,901,664 B2 | 2/2018 | Askem | |
| D813,374 S | 3/2018 | Bjelovuk et al. | |
| D814,016 S | 3/2018 | Bjelovuk et al. | |
| 9,923,401 B2 | 3/2018 | Jung | |
| D815,726 S | 4/2018 | Bjelovuk et al. | |
| D815,727 S | 4/2018 | Bjelovuk et al. | |
| D820,980 S | 6/2018 | Maurice | |
| 10,124,093 B1 | 11/2018 | Francis et al. | |
| 10,143,785 B2 | 12/2018 | Adams et al. | |
| 10,155,070 B2 | 12/2018 | Childress et al. | |
| D842,460 S | 3/2019 | Gierse et al. | |
| D851,759 S | 6/2019 | Jones et al. | |
| D852,356 S | 6/2019 | Steele et al. | |
| 10,328,188 B2 | 6/2019 | Deutsch et al. | |
| D888,225 S | 6/2020 | Askem | |
| 10,682,446 B2 | 6/2020 | Askem et al. | |
| 10,737,002 B2 | 8/2020 | Askem et al. | |
| 11,559,619 B2 | 1/2023 | Adams et al. | |
| 2002/0013545 A1 | 1/2002 | Soltanpour et al. | |
| 2002/0030002 A1 | 3/2002 | Verkaart et al. | |
| 2002/0098097 A1 | 7/2002 | Singh | |
| 2002/0161317 A1 | 10/2002 | Risk et al. | |
| 2004/0068224 A1 | 4/2004 | Couvillon, Jr. et al. | |
| 2005/0234485 A1 | 10/2005 | Seegert et al. | |
| 2006/0281398 A1 | 12/2006 | Yokomizo et al. | |
| 2007/0219513 A1 | 9/2007 | Lina et al. | |
| 2008/0005000 A1 | 1/2008 | Radl et al. | |
| 2008/0234641 A1 | 9/2008 | Locke et al. | |
| 2009/0085527 A1 | 4/2009 | Odaohhara | |
| 2009/0216205 A1 | 8/2009 | Ryan et al. | |
| 2009/0299306 A1 | 12/2009 | Buan | |
| 2010/0022990 A1 | 1/2010 | Karpowicz et al. | |
| 2010/0155465 A1 | 6/2010 | Mollstam et al. | |
| 2010/0244780 A1 | 9/2010 | Turner et al. | |
| 2011/0006876 A1 | 1/2011 | Moberg et al. | |
| 2011/0060300 A1 | 3/2011 | Weig et al. | |
| 2011/0076170 A1 | 3/2011 | Fujisaki et al. | |
| 2011/0077605 A1 | 3/2011 | Karpowicz et al. | |
| 2011/0196291 A1 | 8/2011 | Vischer et al. | |
| 2012/0078181 A1 | 3/2012 | Smith et al. | |
| 2012/0109083 A1 * | 5/2012 | Coulthard ............... A61F 13/05 604/319 | |
| 2012/0289913 A1 | 11/2012 | Eckstein et al. | |
| 2013/0012772 A1 | 1/2013 | Gunday et al. | |
| 2013/0025692 A1 | 1/2013 | Heide et al. | |
| 2013/0053795 A1 | 2/2013 | Coulthard et al. | |
| 2013/0131616 A1 | 5/2013 | Locke | |
| 2013/0237937 A1 | 9/2013 | Ramella et al. | |
| 2013/0270166 A1 | 10/2013 | Locke et al. | |
| 2013/0274718 A1 | 10/2013 | Yao et al. | |
| 2014/0023533 A1 | 1/2014 | Ishii et al. | |
| 2014/0276488 A1 | 9/2014 | Locke et al. | |
| 2015/0174320 A1 | 6/2015 | Grant et al. | |
| 2015/0196765 A1 | 7/2015 | Marnfeldt et al. | |

(56) References Cited

U.S. PATENT DOCUMENTS

| | | |
|---|---|---|
| 2015/0231021 A1 | 8/2015 | Smith et al. |
| 2015/0246164 A1 | 9/2015 | Heaton et al. |
| 2015/0320916 A1 | 11/2015 | Croteau et al. |
| 2016/0015872 A1 | 1/2016 | Luckemeyer et al. |
| 2016/0015957 A1 | 1/2016 | Tieck et al. |
| 2016/0101278 A1 | 4/2016 | Norris et al. |
| 2016/0120706 A1 | 5/2016 | Collinson |
| 2016/0213843 A1 | 7/2016 | Despa et al. |
| 2016/0250398 A1 | 9/2016 | Barr et al. |
| 2016/0262672 A1 | 9/2016 | Hammond |
| 2016/0271305 A1 | 9/2016 | Kurihara et al. |
| 2016/0303358 A1 | 10/2016 | Croizat et al. |
| 2017/0165405 A1 | 6/2017 | Muser et al. |
| 2017/0189588 A1 | 7/2017 | Croizat et al. |
| 2017/0189666 A1 | 7/2017 | Sealfon et al. |
| 2017/0216501 A1 | 8/2017 | Armstrong et al. |
| 2017/0224975 A1 | 8/2017 | Peer et al. |
| 2017/0296716 A1 | 10/2017 | Middleton et al. |
| 2017/0319758 A1 | 11/2017 | Eddy et al. |
| 2017/0354767 A1 | 12/2017 | Carr et al. |
| 2018/0001000 A1 | 1/2018 | Herwig et al. |
| 2018/0021178 A1 | 1/2018 | Locke et al. |
| 2018/0104391 A1 | 4/2018 | Luxon et al. |
| 2018/0140466 A1 | 5/2018 | Hunt |
| 2018/0250459 A1 | 9/2018 | Kimball et al. |
| 2018/0318476 A1 | 11/2018 | Askem et al. |
| 2019/0021541 A1 | 1/2019 | Kuempel |
| 2019/0192744 A1 | 6/2019 | Greener et al. |
| 2019/0358372 A1 | 11/2019 | Askem et al. |
| 2020/0121833 A9 | 4/2020 | Askem et al. |
| 2021/0077670 A1 * | 3/2021 | Long ..................... A61M 1/73 |
| 2021/0392761 A1 | 12/2021 | Kitagawa et al. |

FOREIGN PATENT DOCUMENTS

| | | |
|---|---|---|
| EP | 2255837 A1 | 12/2010 |
| EP | 3124059 A1 | 2/2017 |
| EP | 3124060 A1 | 2/2017 |
| FR | 2939320 A1 | 6/2010 |
| GB | 1220857 A | 1/1971 |
| JP | S5647279 U | 4/1981 |
| JP | H01101978 A | 4/1989 |
| JP | H0796029 A | 4/1995 |
| JP | 2007218241 A | 8/2007 |
| JP | 6047279 B2 | 12/2016 |
| WO | WO-9605873 A1 | 2/1996 |
| WO | WO-0061206 A1 | 10/2000 |
| WO | WO-03081762 A1 | 10/2003 |
| WO | WO-03101508 A2 | 12/2003 |
| WO | WO-2008033788 A2 | 3/2008 |
| WO | WO-2009071924 A1 | 6/2009 |
| WO | WO-2009144726 A1 | 12/2009 |
| WO | WO-2011075706 A1 | 6/2011 |
| WO | WO-2011094410 A2 | 8/2011 |
| WO | WO-2012004298 A1 | 1/2012 |
| WO | WO-2012100624 A1 | 8/2012 |
| WO | WO-2013064852 A1 | 5/2013 |
| WO | WO-2013078214 A1 | 5/2013 |
| WO | WO-2014115819 A1 | 7/2014 |
| WO | WO-2014164655 A1 | 10/2014 |
| WO | WO-2015197462 A1 | 12/2015 |
| WO | WO-2016018448 A1 | 2/2016 |
| WO | WO-2016103031 A1 | 6/2016 |
| WO | WO-2016109048 A1 | 7/2016 |
| WO | WO-2017027850 A1 * | 2/2017 | .............. A61M 1/96 |
| WO | WO-2017044138 A1 | 3/2017 |
| WO | WO-2017062042 A1 | 4/2017 |
| WO | WO-2017160412 A1 | 9/2017 |
| WO | WO-2017197357 A1 | 11/2017 |
| WO | WO-2018009873 A1 | 1/2018 |
| WO | WO-2018009880 A1 | 1/2018 |
| WO | WO-2018041854 A1 | 3/2018 |
| WO | WO-2018150263 A1 | 8/2018 |
| WO | WO-2018150267 A2 | 8/2018 |
| WO | WO-2018167199 A1 | 9/2018 |
| WO | WO-2018185101 A1 | 10/2018 |
| WO | WO-2018195101 A1 | 10/2018 |
| WO | WO-2019063467 A1 | 4/2019 |
| WO | WO-2019129581 A2 | 7/2019 |
| WO | WO-2019139829 A1 | 7/2019 |
| WO | WO-2019179943 A1 | 9/2019 |
| WO | WO-2019211730 A1 | 11/2019 |
| WO | WO-2019211731 A1 | 11/2019 |
| WO | WO-2019211732 A1 | 11/2019 |
| WO | WO-2019224059 A1 | 11/2019 |
| WO | WO-2020011690 A1 | 1/2020 |

OTHER PUBLICATIONS

International Search Report and Written Opinion for Application No. PCT/IB2019/053508, mailed on Aug. 7, 2019, 11 pages.

Jenkins R.W., et al., "Mechanisms of Resistance to Immune Checkpoint Inhibitors," British Journal of Cancer, Jan. 2, 2018, vol. 118, https://doi.org/10.1038/bjc.2017.434 , pp. 9-16.

Wikipedia, "Battery Charger," retrieved from https://web.archive.org/web/20181109005000/https://en.wikipedia.org/wiki/Battery_charger , on Nov. 9, 2018, 12 pages.

* cited by examiner

100

300A

150G

160G

161G

Canister & Canister-free mode
Escalation of leak alert

8102

| Sustainable air leak occurs in the system |
|---|
| Occurs due to a high air leak in the system e.g. dressing is not fully sealed. The pump will remain on while alerting, attempting to continue NPWT. |

8104

| Minor leak alert |
|---|
| The pump module is delivering NPWT with a high duty cycle. Battery life is reduced, but the pump continues to deliver therapy. |

|  |  | NTWT ON<br>Buzzer ON |
|---|---|---|

8106

| Leak deteriorates |
|---|
| Air leak deteriorates, and the leak becomes catastrophic/unsustainble. The pump is required to be ON at a 99%+ duty cycle. The pump cannot achieve pressure therefore the user is not gaining any benefit from the pump attempting to deliver therapy. |

8110

| Major leak alert |
|---|
| The pump cannot achieve pressure therefore the user is not gaining any benefit from the pump attempting to deliver therapy. |

| 8112  | 8114 | NTWT OFF<br>Buzzer ON |
|---|---|---|

8108

| Unsustainable air leak occurs |
|---|
| Catastrophic air leak during the MC, e.g.dressing removed/disconnected. The pump cannot achive pressure therefore the user is not gaining any benefit from the pump attempting to deliver therapy. |

FIG. 8A

Canister mode only
Escalation blockage alert

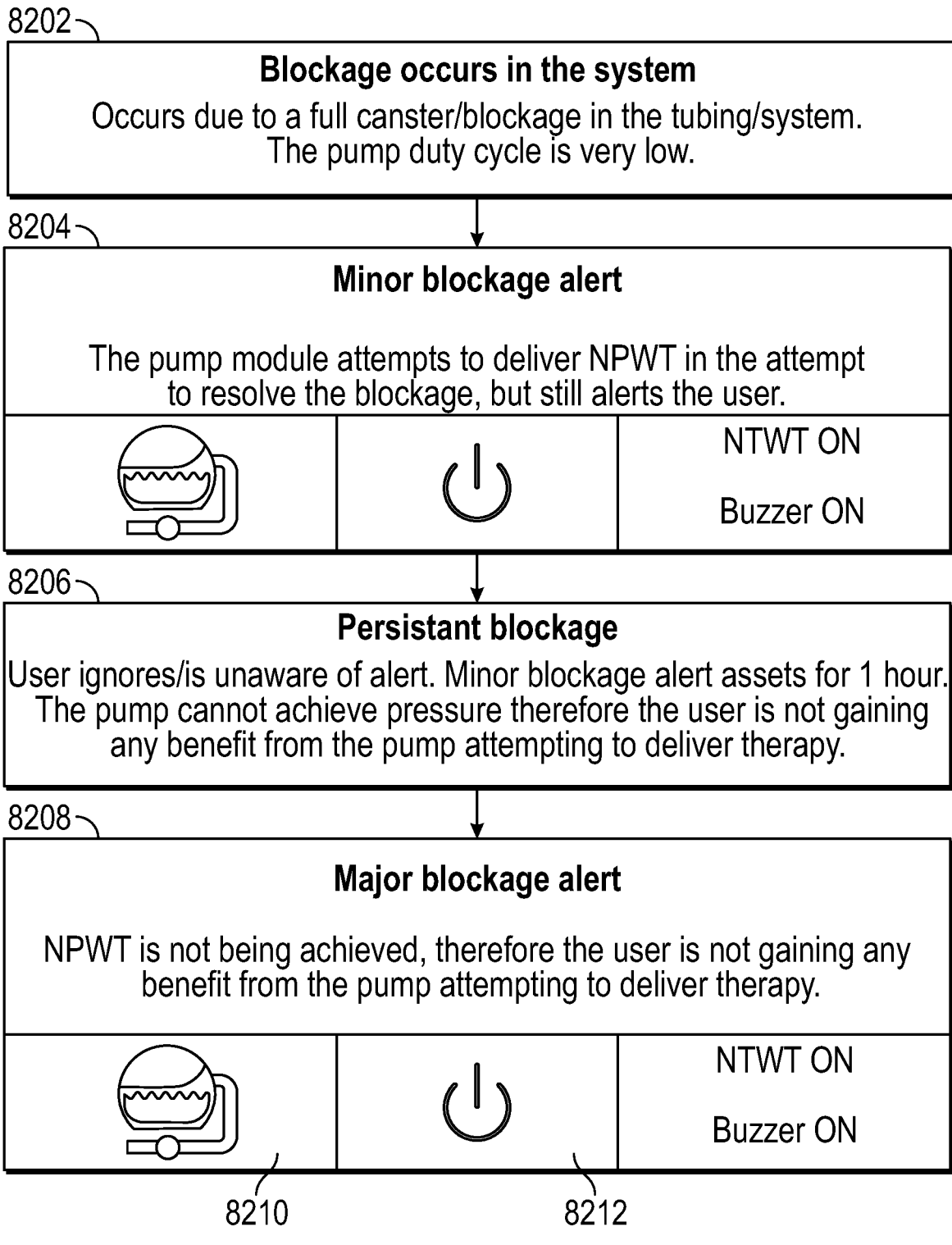

8202

Blockage occurs in the system

Occurs due to a full canster/blockage in the tubing/system.
The pump duty cycle is very low.

8204

Minor blockage alert

The pump module attempts to deliver NPWT in the attempt
to resolve the blockage, but still alerts the user.

| | | NTWT ON |
| | | |
| | | Buzzer ON |

8206

Persistant blockage

User ignores/is unaware of alert. Minor blockage alert assets for 1 hour.
The pump cannot achieve pressure therefore the user is not gaining
any benefit from the pump attempting to deliver therapy.

8208

Major blockage alert

NPWT is not being achieved, therefore the user is not gaining any
benefit from the pump attempting to deliver therapy.

| | | NTWT ON |
| | | |
| | | Buzzer ON |

SYSTEMS AND METHODS FOR CONTROLLING DUAL MODE NEGATIVE PRESSURE WOUND THERAPY APPARATUS

CROSS-REFERENCE TO RELATED APPLICATIONS

This application is a continuation of U.S. application Ser. No. 17/043,519, filed Sep. 29, 2020, and issued as U.S. Pat. No. 11,559,619, which is a U.S. national stage application of International Patent Application No. PCT/IB2019/053508, filed Apr. 29, 2019, which claims the benefit of U.S. Provisional Application No. 62/664,688, filed Apr. 30, 2018, each of which is hereby incorporated by reference in its entirety.

FIELD

Embodiments or arrangements disclosed herein relate to methods and apparatuses for dressing and treating a wound with topical negative pressure (TNP) therapy. For example, but without limitation, any embodiments disclosed herein may relate to treating a wound with reduced pressure. As another non-limiting example, any of the embodiments disclosed herein may relate to apparatuses and methods for controlling the operation of a TNP system.

DESCRIPTION OF RELATED ART

Many different types of wound dressings are known for aiding in the healing process of a human or animal. These different types of wound dressings include many different types of materials and layers, for example, pads such as gauze pads or foam pads. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue edema; encouraging blood flow; stimulating the formation of granulation tissue; removing excess exudates, and may reduce bacterial load and thus reduce the potential for infection of the wound. Furthermore, TNP therapy permits less outside disturbance of the wound and promotes more rapid healing.

SUMMARY

In some embodiments, a negative pressure wound therapy device includes a negative pressure source configured to provide negative pressure to a wound via a fluid flow path including a wound dressing positioned over the wound and a controller configured to operate the negative pressure source to provide negative pressure to the wound when the negative pressure source is fluidically connected to the wound dressing directly or when the negative pressure source is fluidically connected to the wound dressing via a canister configured to store at least some fluid aspirated from the wound by the negative pressure source. The controller can be further configured to: in response to determining that the negative pressure source is directly fluidically connected to the wound dressing, operate the negative pressure source in a first mode to provide negative pressure to the wound; in response to determining that the negative pressure source is fluidically connected to the wound dressing via the canister, operate the negative pressure source in a second mode to provide negative pressure to the wound, the second mode being different from the first mode; determine a level of activity of the negative pressure source; in response to determining that the level of activity of the negative pressure source over a first duration of time satisfies at least one of a leak condition or a blockage condition, provide a first indication of at least one of a leak or a blockage in the fluid flow path after expiration of the first duration of time; and in response to determining that the level of activity of the negative pressure source does not satisfy the at least one of the leak condition or the blockage condition over a second duration of time subsequent to the first duration of time, discontinue provision of the first indication of the at least one of the leak or the blockage in the fluid flow path after expiration of the second duration of time.

In certain embodiments, the apparatus of preceding paragraph can include one or more of the following features. The second duration of time can be shorter than the first duration of time. The level of activity of the negative pressure source can include duty cycle of the negative pressure source. At least one of the leak condition or the blockage condition can include a first duty cycle threshold in the first mode and a second duty cycle threshold in the second mode, the first duty cycle threshold different from the second duty cycle threshold. The controller can be further configured to compare the level of activity over the first and second durations of time to one of the first or second duty cycle thresholds. The first duty cycle threshold can be greater than the second duty cycle threshold.

In some implementations, the apparatus of any of preceding paragraphs can include one or more of the following features. The controller can be further configured to provide the first indication of the at least one of the leak or blockage in the fluid flow path without deactivating the negative pressure source. In response to determining that the level of activity of the negative pressure source continues to satisfy the at least one of the leak condition or the blockage condition over a third duration of time subsequent to the first duration of time, the controller can be configured to deactivate the negative pressure source after expiration of the third duration of time. The controller can be further configured to provide a second indication different from the first indication after expiration of the third duration of time. The first indication can include a visual indication of a first color and the second indication can include a visual indication of a second color different from the first color. The third duration of time can be subsequent to the second duration of time.

In some embodiments, a method of using or operating the device having any combination of features described in one or more preceding paragraphs is provided.

In certain embodiments, a method operating a negative pressure wound therapy device including a negative pressure source and a controller includes, by the controller: operating the negative pressure source configured to provide negative pressure to a wound via a fluid flow path comprising a wound dressing positioned over the wound when the negative pressure source is fluidically connected to the wound dressing directly or when the negative pressure source is fluidically connected to the wound dressing via a canister configured to store at least some fluid aspirated from the wound by the negative pressure source; in response to determining that the negative pressure source is directly fluidically connected to the wound dressing, operating the negative pressure source in a first mode to provide negative pressure to the wound; in response to determining that the negative pressure source is fluidically connected to the wound dressing via the canister, operating the negative pressure source in a second mode to provide negative pressure to the wound, the second mode being different from the first mode; determining a level of activity of the negative pressure source; in response to determining that the level of activity of the negative pressure source over a first duration of time satisfies at least one of a leak condition or a blockage condition, providing a first indication of at least one of a leak or a blockage in the fluid flow path after expiration of the first duration of time; and in response to determining that the level of activity of the negative pressure source does not satisfy the at least one of the leak condition or the blockage condition over a second duration of time subsequent to the first duration of time, discontinuing provision of the first indication of the at least one of the leak or the blockage in the fluid flow path after expiration of the second duration of time.

In some implementations, the method of preceding paragraph can include one or more of the following features. The second duration of time can be shorter than the first duration of time. The level of activity of the negative pressure source can include duty cycle of the negative pressure source. At least one of the leak condition or the blockage condition comprises a first duty cycle threshold in the first mode and a second duty cycle threshold in the second mode, the first duty cycle threshold different from the second duty cycle threshold. The method can further include, by the controller, comparing the level of activity over the first and second durations of time to one of the first or second duty cycle thresholds. The first duty cycle threshold can be greater than the second duty cycle threshold.

In certain embodiments, the method of any of preceding paragraphs can include one or more of the following features. The method can include, by the controller, providing the first indication of the at least one of the leak or blockage in the fluid flow path without deactivating the negative pressure source, and in response to determining that the level of activity of the negative pressure source continues to satisfy the at least one of the leak condition or the blockage condition over a third duration of time subsequent to the first duration of time, deactivating the negative pressure source after expiration of the third duration of time. The method can include, by the controller, providing a second indication different from the first indication after expiration of the third duration of time. The first indication can include a visual indication of a first color and the second indication comprises a visual indication of a second color different from the first color. The third duration of time can be subsequent to the second duration of time.

BRIEF DESCRIPTION OF THE DRAWINGS

Other features and advantages of the present disclosure will be apparent from the following detailed description, taken in conjunction with the accompanying drawings of which:

FIGS. 8A and 8B illustrate escalation of blockage and leak alerts according to some embodiments.

DETAILED DESCRIPTION

Overview

Embodiments disclosed in this section or elsewhere in this specification relate to apparatuses and methods of treating a wound with reduced pressure, including pump and wound dressing components and apparatuses. The apparatuses and components comprising the wound overlay and packing materials, if any, are sometimes collectively referred to in this section or elsewhere in this specification as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, electrical burns, diabetic ulcers, pressure ulcers, stoma, surgical wounds, trauma and venous ulcers or the like.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue edema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Dual Mode Negative Pressure System

Figure 1:
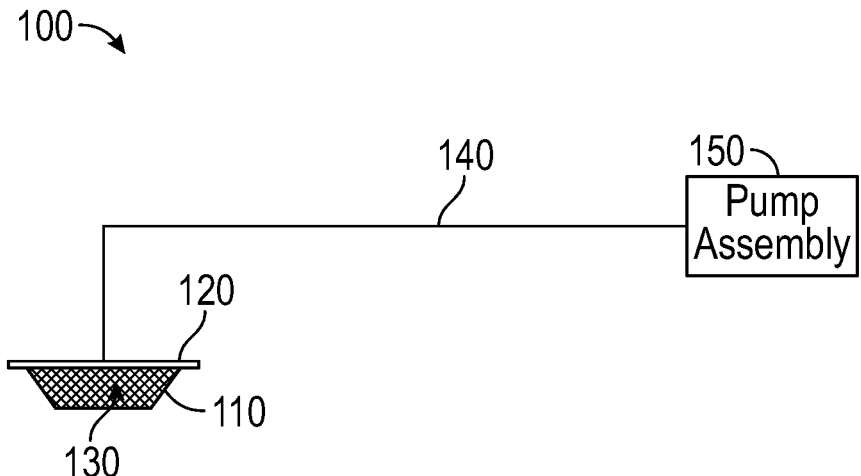
FIG. 1 illustrates a reduced pressure wound therapy system including a pump assembly according to some embodiments.

FIG. 1 illustrates a negative or reduced pressure wound treatment (or TNP) system 100 according to some embodiments. The system 100 comprises a wound filler 130 placed inside a wound cavity 110, the wound cavity 110 sealed by a wound cover 120. In some embodiments, one or more of the wound filler 130, the wound cover 120, or any other component, such as a contact layer (not shown), make up a wound dressing. The system 100 includes a negative pressure wound therapy device, apparatus, or a pump assembly 150 configured to provide reduced pressure to the wound. For example, a conduit 140 having at least one lumen can provide a fluid flow path between the pump assembly 150 and the wound.

Figure 2A:
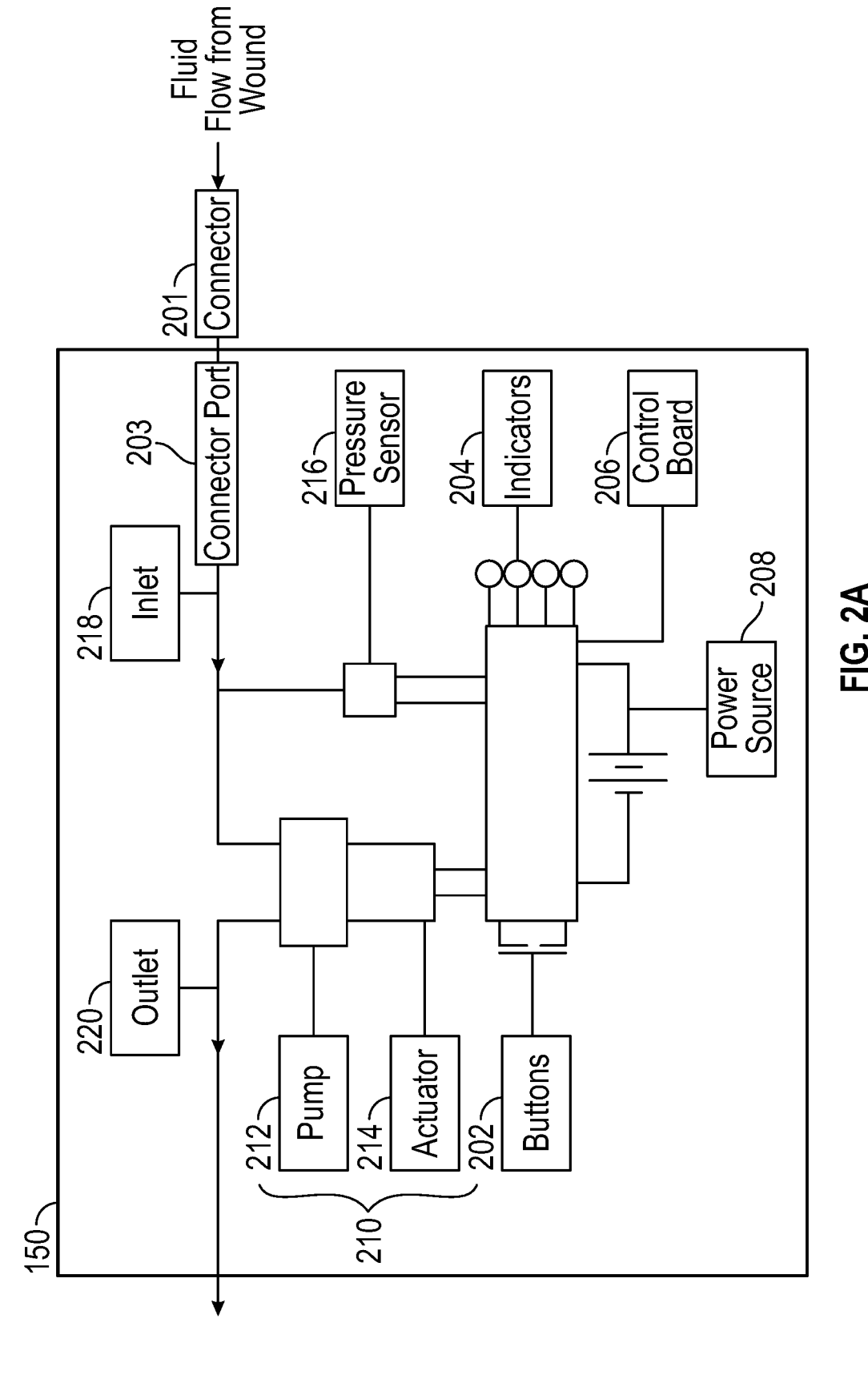
FIG. 2A illustrates a dual mode reduced pressure wound therapy system operating in a canisterless mode of operation according to some embodiments.
Figure 2B:
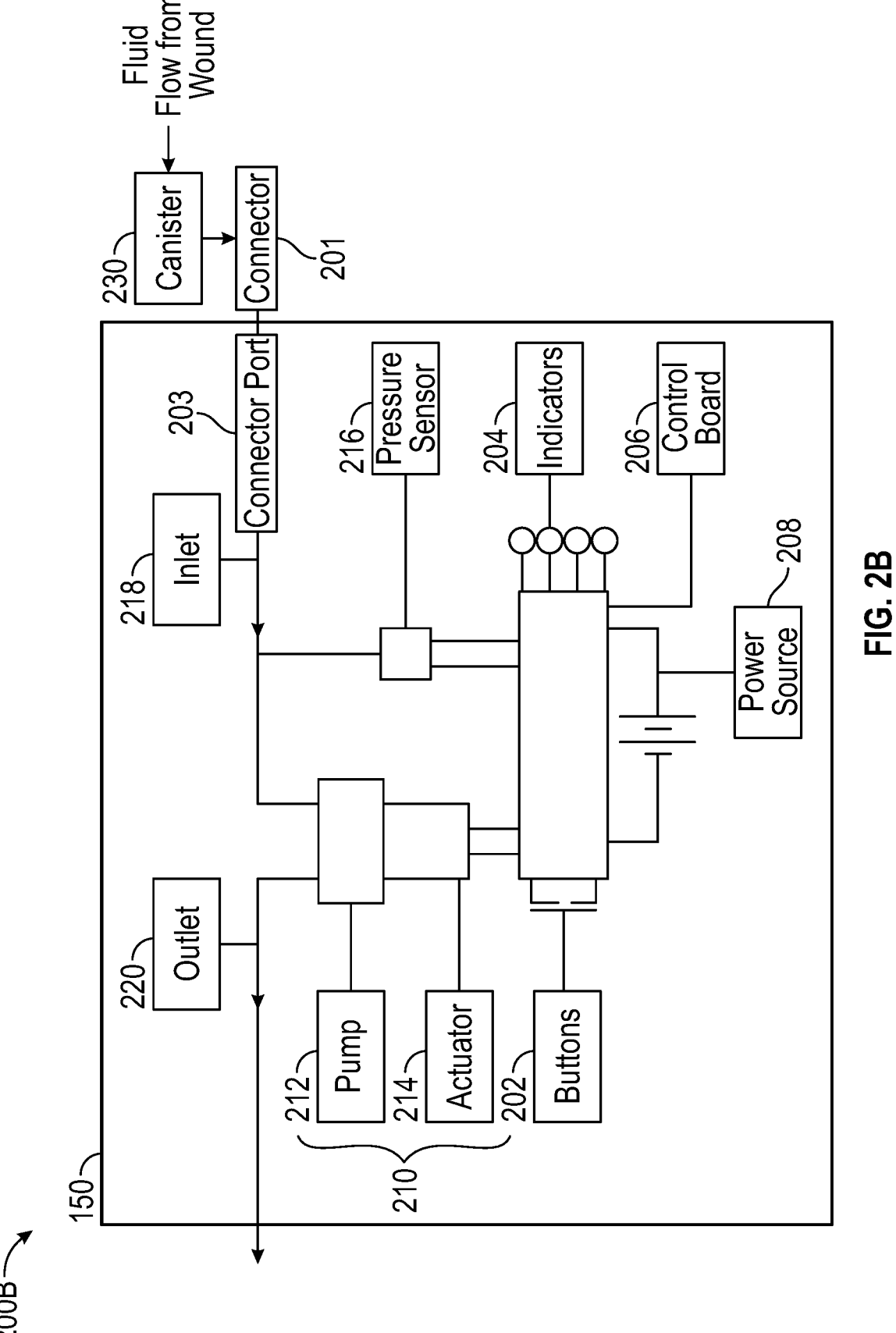
FIG. 2B illustrates a dual mode reduced pressure wound therapy system operating in a canister mode of operation according to some embodiments.

FIGS. 2A-2B illustrate that the reduced pressure wound therapy system can be configured to operate with and without a canister (for example, in canister and canisterless modes) according to some embodiments. FIG. 2A shows an embodiment of the TNP system 200A that has a wound dressing connected directly to the pump assembly 150 (for example, canisterless mode). FIG. 2B shows an embodiment of the TNP system 200B that has a canister 230 interposed between the wound dressing and the pump assembly 150 (for example, canister mode). At the beginning of the application of negative pressure wound therapy to a wound when the wound is in the early stages of the healing process and exudes a significant volume of exudate, the reduced pressure wound therapy system may operate with a canister. In this mode of operation, the negative pressure wound therapy system may operate with a foam or gauze RENA-SYS™ dressing sold by Smith & Nephew or any other suitable dressing. Operation of the reduced pressure wound therapy system with a canister may sometimes be referred to herein as "RENASYS", "RENASYS-mode", or derivatives thereof. As the wound is progressing through the healing process and is starting to exude a smaller volume of exudate, the canister may be removed and the negative pressure wound therapy system may operate with an absorbent dressing, such as the PICO™ dressing sold by Smith & Nephew or any other suitable dressing that retains the wound exudate within the dressing. Operation of the reduced pressure wound therapy system without a canister may sometimes be referred to herein as "PICO", "PICO-mode", or derivatives thereof.

The pump assembly 150 can include one or more switches or buttons 202, one or more indicators 204, and a control board 206, which can include one or more controllers, one or more memories, or the like. The one or more buttons 202 and the one or more indicators 204 (which collectively make up a user interface) can be in electrical communication with the control board 206, which can include one or more controllers and memory. The one or more buttons 202 can be used for any suitable purpose for controlling an operation of the pump assembly 150. For example, the one or more buttons 202 can be used to activate the pump system 150, pause the pump assembly 150, and clear system indicators such as one or more of the one or more indications 204. The one or more buttons 202 can by any type of switch or button, such as a touchpad, touch screen, keyboard, and so on. In some embodiments, the one or more buttons 202 can be a press button. In various implementations, one or more buttons 202 can be included on a touchscreen interface.

The pump assembly 150 can include a connector port 203 adapted to receive a connector 201. The connector 201 can be a part of the canister or the wound dressing that is attached to the pump assembly 150, as described herein. The connector 201 can be removably attached to the connector port 203. In some arrangements, a first connector 201 can be removed from the pump assembly 150 and replaced with a second connector 201 that is then attached to the pump assembly 150. For example, a first connector 201 that is connected to a RENASYS™ dressing can be removed from the connector port 203 and replaced with a second connector 201 that connected to a PICO™ dressing, thereby allowing the pump assembly 150 to be switched from canister to a canisterless mode of operation. As described in more detail below, the connector 201 and/or pump assembly 150 can be adapted to allow the pump assembly 150 to detect whether a canister or canisterless connector 201 is attached to the connector port 203. In some arrangements, the operation of the pump assembly 150 can be adjusted according to whether the pump assembly 150 detects a canister or a canisterless connector 201 is connected to the connector port 203.

In some embodiments, the connector port 203 can include one or more connector switches in electrical communication with the control board 206, which can include one or more controllers. The one or more connector switches can be configured to engage one or more connectors of the canister or the dressing. In some embodiments, the one or more connector switches can advantageously permit the pump assembly 150 (e.g., the control board 206) to differentiate between a canister connection and a dressing connection. In some embodiments, one or more of the connectors 201 can include one or more connector switches in addition to or in lieu of the one or more connector switches of the connector port 203. The connector switches contemplated herein can be mechanical, electrical, optical, and/or magnetic, or any other suitable switch, and can include sensors and the like. The connector switches can be configured to close or open an electrical circuit, thereby permitting the control board 206 to detect whether the connector switch is engaged or disengaged. For example, as described in more detail below, the connector port 203 can include a connector switch that is actuated by a portion of a connector 201 that couples a canister to the connector port 203. The connector switch can be further configured so that the switch is not actuated by a connector 201 that couples a dressing to the connector port 203, thereby allowing the control board 206 to detect whether a canister or a dressing is attached to the connector port 203. In some arrangements, the pump assembly 150 can be configured so that the connector switch is activated by a connector 201 that couples a dressing to the connector port 203 and is not activated by a connector 201 that couples a canister to the connector port 203.

With continued reference to FIG. 2A, the one or more indicators 204 can indicate one or more operating or failure conditions of the pump assembly 150. Each of the one or more indicators 204 may provide an indication regarding a different operating or failure condition. In some implementations, an active (such as, lit) visual indicator (such as, LED) of the one or more indicators 204 can represent a certain operation condition for the pump assembly 150. For example, a dressing indicator of the one or more indicators 204 can provide an indication as to presence of leakages or leaks in the TNP system 100, and an active dressing indicator can represent a leak. As another example, a dressing capacity indicator of the one or more indicators 204 can provide an indication as to the remaining fluid capacity of the wound dressing or canister, and an active dressing capacity indicator can represent that the wound dressing or canister is at or nearing capacity. As yet another example, a power source indicator of the one or more indicators 204 can provide an indication as to remaining capacity or life of the power source 208, such as one or more batteries, and an active power source indicator can represent a low capacity. In some embodiments, the one or more indicators 204 can represent a combination of one or more of the above operating or failure conditions of the pump assembly 150 or other operating or failure conditions for the pump assembly 150.

In some implementations, the one or more indicators 204 can be icons. For example, the one or more indicators 204 can be activated (e.g., lit) via an illumination source such as LEDs (not shown) of pump assembly 150. The one or more indicators 204 can, for instance, be of a different color, two different colors (e.g., two indicators can share the same color), or same color. In some embodiments, the pump assembly 150 can include visual, audible, tactile, haptic, or other types of indicators or alarms configured to signal to the user various operating conditions. Such conditions include system on/off, standby, pause, normal operation, dressing problem, leak, error, and the like. The indicators can include speakers, displays, light sources, etc., or combinations thereof. In various implementations, one or more buttons indicators 204 can be included on a touchscreen interface.

The pump assembly 150 can be powered by a power source 208 such as a one or more battery cells or any other suitable power source. Battery cells can include any combination of one or more of lithium-ion, lithium-polymer, lithium iron phosphate, lead acid, nickel based, alkaline, or the like. The pump assembly 150 can also include a source of negative pressure 210, which can include a pump 212 powered by an actuator 214, such as an electric motor. In some embodiments, the actuator 214 is integrated into the pump 212. The negative pressure source 210 can be a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, a pump operated by a voice coil actuator, or any other suitable pump or micropump or any combinations of the foregoing, The pump assembly 150 can also include one or more pressure sensors 216 that measure pressure in the fluid flow path. The power source 208 can supply power to electro-mechanical components of the pump assembly 150, including one or more of the negative pressure source 210, pressure sensor 216, control board 206, buttons 202, and indicators 204.

The pump assembly 150 can further include an inlet 218 to connect the pump assembly 150 to the wound dressing. For example, the inlet 218 can be connected to the connector port 203 and the connector 201 that is in fluid communication with the wound dressing via a fluid flow path.

The pump assembly 150 can also include an outlet 220. The outlet 220 can vent or exhaust gas to the atmosphere. In some embodiments, a filter (not shown) can be interposed between the outlet 220 and the atmosphere. The filter can provide filtration of the gas prior to venting the gas to the atmosphere. The filter can be a bacterial filter, odor filter, or any combination thereof. In some embodiments, a dampening component (not shown), such as a noise dampening component, can be interposed between the outlet 220 and the atmosphere. The dampening component can reduce the noise generated by the pump assembly 150 during operation. In some implementations, the pump assembly 150 can communicate information, such as information related to provision of negative pressure therapy, to one or more remote devices. Such communication can be performed using a wired or wireless interface.

FIG. 2B illustrates the pump assembly 150 of FIG. 2A with a canister 230 additionally positioned in a fluid flow path between the inlet 218 and the wound dressing. In the illustrated embodiment, the connector 201 fluidically connects the canister 230 to the connector port 203. As discussed further below, the connector 201 can be configured to signal to the pump assembly 150 whether the connector port 203 is connected to a wound dressing directly or whether a canister 230 is disposed between the connector 203 and the wound dressing.

In some embodiments, the control board 206 (for example, a controller) adjusts one or more operational parameters of negative pressure wound therapy depending on whether the pump assembly is connected to the canister or the dressing. For example, in canisterless mode, the level of negative pressure provided to the wound can be reduced compared to canister mode because the wound is exuding a smaller amount of fluid. As another example, detection of one or more operating conditions can be enabled, disabled, or adjusted. For instance, in canisterless mode, canister full detection (or blockage detection) and alarming can be disabled and, instead, dressing full detection and alarming can be enabled.

In some embodiments, the pump assembly 150 includes a user interface, such as one or more displays, indicators, lights, buttons, switches, speakers, vibrating elements, etc. The user interface can be adjusted based on detection of a canister. For example, in canister mode, the user interface can include an indicator alerting a user when canister becomes full. In canisterless mode, this indicator can be replaced with an indicator alerting the user when the dressing become full. In some embodiments, the indicators are icons.

Figure 3A:
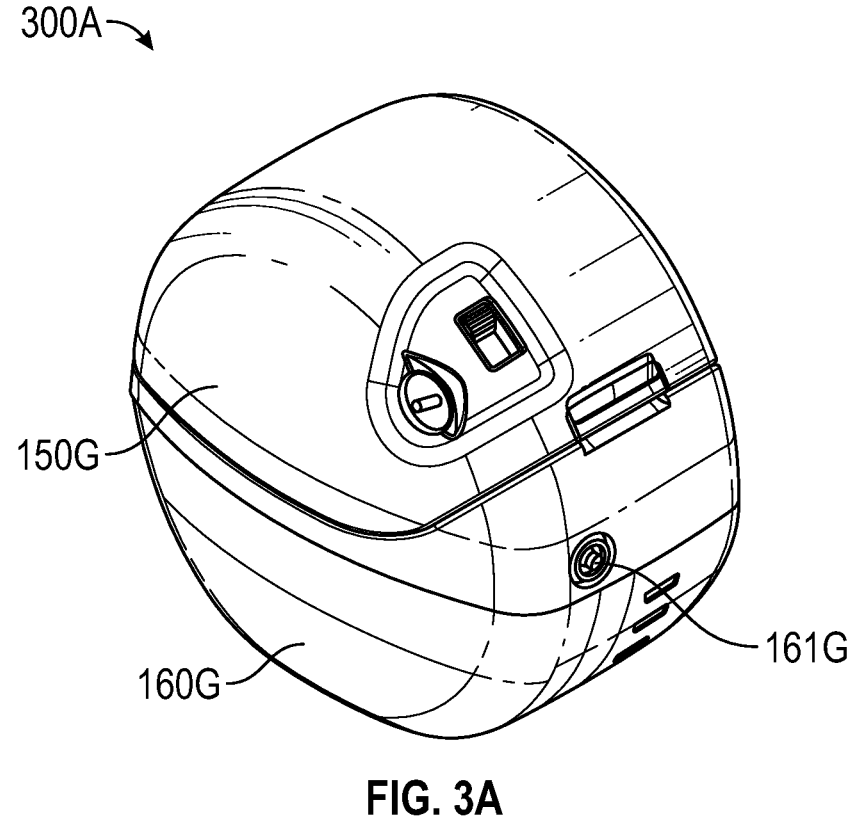
FIGS. 3A and 3B illustrate a dual mode reduced pressure wound therapy apparatus according to some embodiments.

FIG. 3A depicts a perspective view 300A of an embodiment of a dual mode TNP system in a canister mode according to some embodiments. In the illustrated system, a canister 160G is attached to a pump assembly 150G (which can be similar as the pump assembly 150 described herein). The pump assembly 150G can be adapted to be slidably coupled to the canister 160G. The canister 160G can have an inlet 161G through which wound exudate can enter the canister 160G. In some embodiments, the pump assembly 150G may slide back to disengage the pump assembly 150G from the canister 160G, as illustrated with respect to FIG. 3B.

Figure 3B:
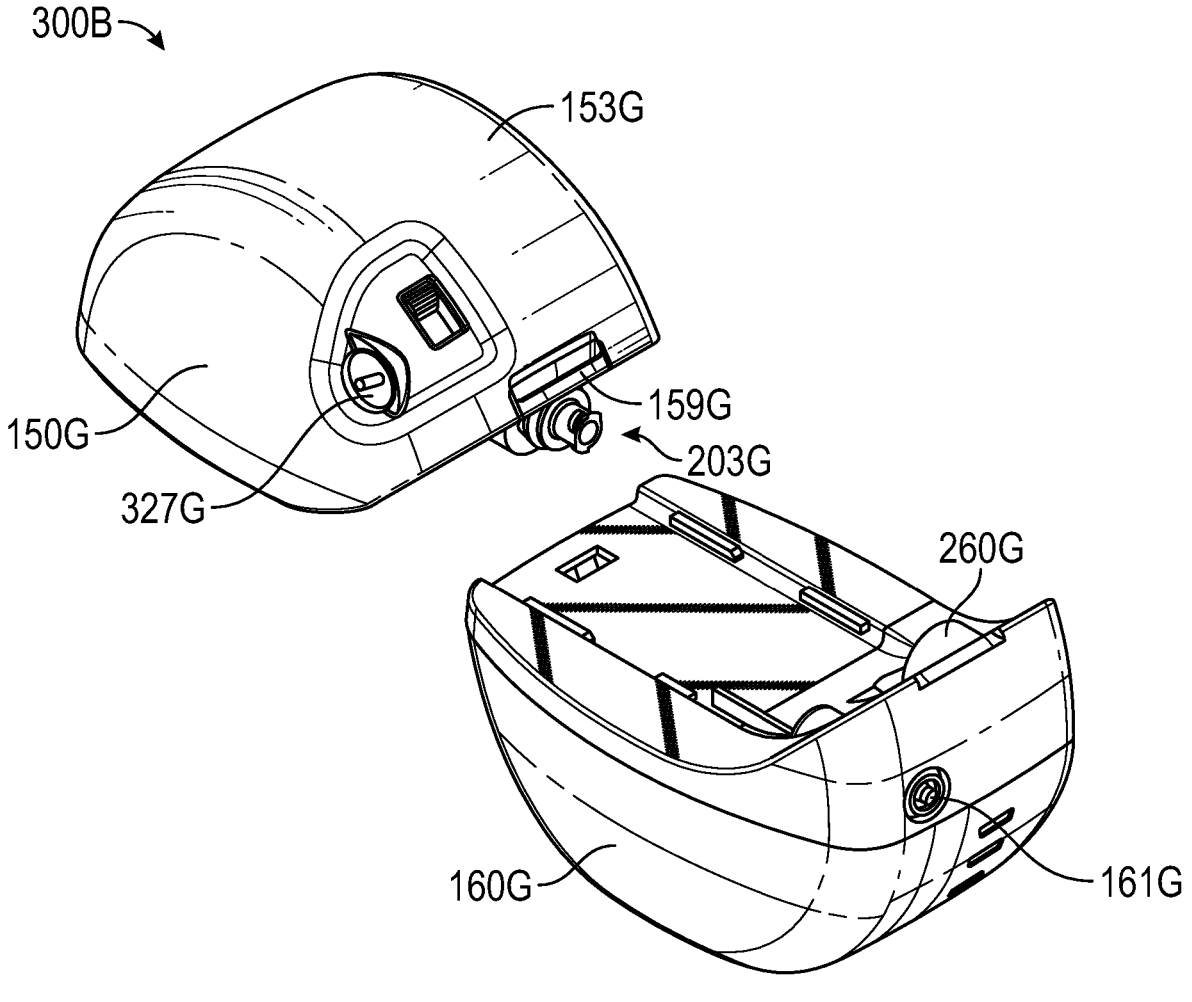

FIG. 3B depicts a perspective view 300B of an embodiment of the TNP system with the canister 160G disengaged from the pump assembly 150G according to some embodiments. In some cases, the pump assembly 150G can operate in a canisterless mode. As described above, the pump assembly 150G can have a connector port 203G that is adapted to connect to a connector 201 (shown schematically in FIGS. 2A-2B). The connector 201 can be a canister connector or a canisterless connector as discussed herein. The connector port 203G can be fluidically connected to a negative pressure source (such as, vacuum pump) housed within the pump assembly 150G. The connector port 203G can establish a flow path between the negative pressure source of the pump assembly 150G and the connector 201 that is connected to the connector port 203G. The pump assembly 150G can provide negative pressure to a canister connector 260G or a canisterless connector that is attached to the connector port 203G. The canister 160G can have the canister connector 260G that fluidically connects to the connector port 203G when the pump assembly 150G is slidably mounted onto the canister 160G. Mounting (such as slidingly mounting) the canister 160G can activate a switch configured to indicate that the canister has been connected, as described herein. Conversely, dismounting of the canister 160G can deactivate the switch. The canister 160G can have an inlet 161G through which wound exudate enters the canister 160G when negative pressure is applied to the canister 160G through the canister connector 260G.

With continued reference to FIGS. 3A-3B, the pump assembly 150G can include a dial 327G (also illustrated in FIGS. 4A-4B) that allows pressure selection on the pump assembly 150G. The magnitude of the negative pressure supplied by the pump assembly 150G can be adjusted by turning the dial 327G. The dial 327G can be adapted to turn to two or more discreet settings. For example, the dial 327G can have three discreet settings that allow the negative pressure provided by the pump assembly 150G to be set to one of three settings (e.g., –60 mmHg, –80 mmHg, and –120 mmHg). The pump assembly 150G can include a bar 159G that can be used as an anchoring site for a strap or clasp, thereby allowing the pump assembly 150G to be suspended from a strap that is attached to the bar 159G. When the canister 160G and the pump assembly 150G are connected together, a ramped portion of the top surface of the canister 160G can form an overhang that is supported on an inclined portion of the bottom surface of the pump assembly 150G, thereby enhancing retention of the canister 160G on the pump assembly 150G when the pump assembly 150G is suspended from the bar 159G. The pump assembly 150G can include one or more icons on the housing 153G of the pump assembly 150G. The icons can be backlit by a light source that is disposed within the housing 153G of the pump assembly 150G.

Operating Dual Mode Negative Pressure System

Figure 4A:
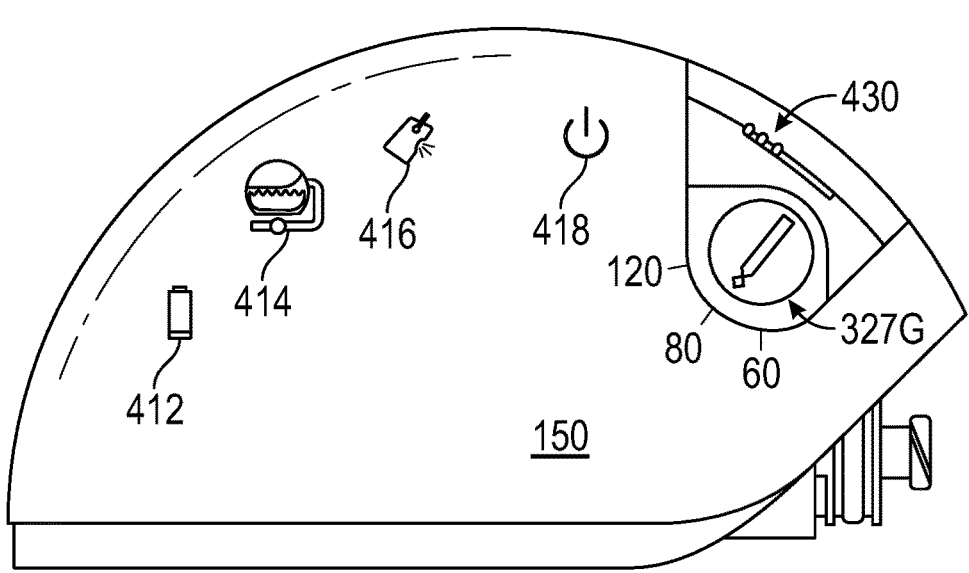
FIGS. 4A and 4B illustrate a dual mode reduced pressure wound therapy apparatus according to some embodiments.
Figure 4B:
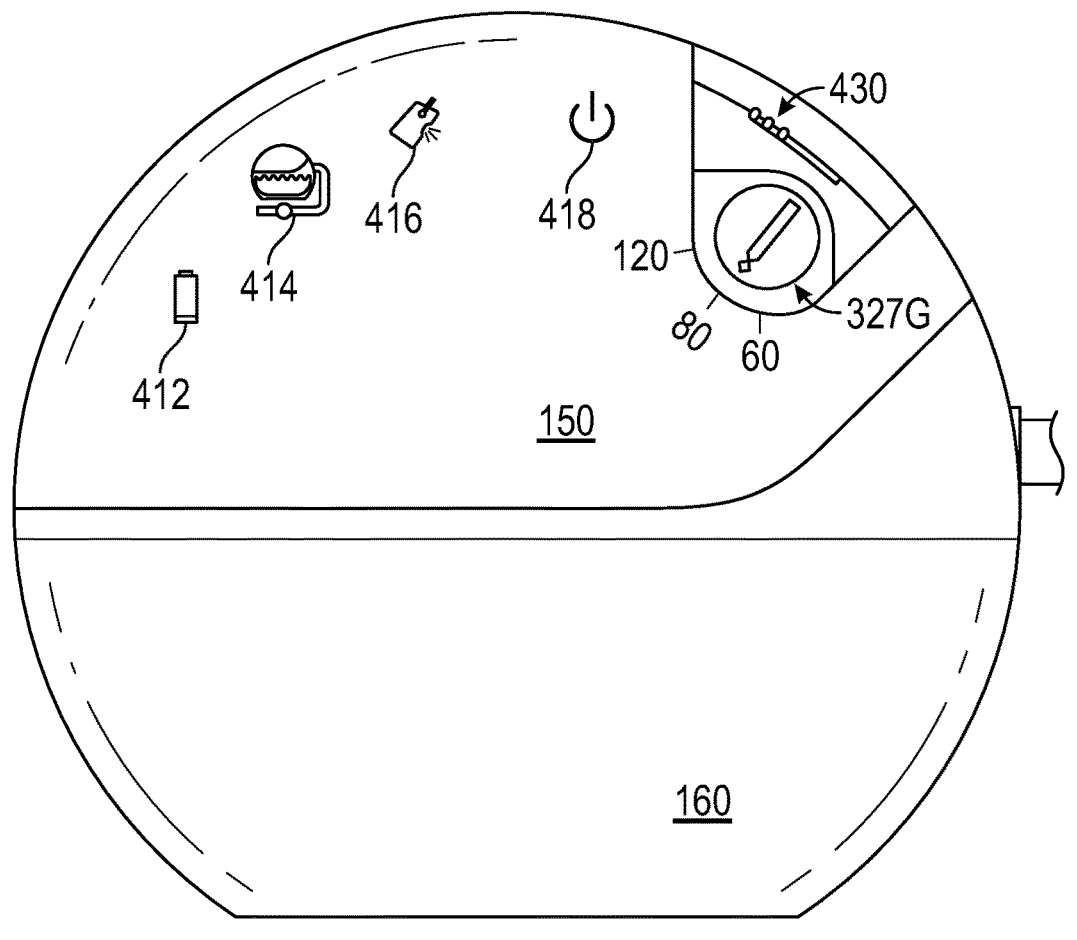

In some embodiments, a dual mode TNP system of any of the embodiments disclosed herein, including a system illustrated in FIGS. 4A and 4B, can be operated or used by a user, such as clinician and/or patient. In particular, use of the TNP system can begin with the assessment of a patient and the wound to be treated. This may be followed by the initial selection of canister or canisterless mode of treatment and dressing or canister size to be used in the selected mode. For example, small or medium foam or medium gauze dressing can be used in canister mode. As another example, small (approximately 10×20 cm), medium (approximately 15×15 cm), or large (approximately 20×20 cm) multi-layer absorbent dressing can be used in canisterless mode.

The operating mode can be changed at any time during use when clinically appropriate, such as switching from canister mode to canisterless mode after the wound has sufficiently healed to exude lower volume of fluid, which can be managed by the absorbent dressing. Switching from canister to canisterless mode can include turning off the source of negative pressure, removing the canister and dressing, applying appropriate different dressing and connecting the dressing to the source of negative pressure, and turning on the source of negative pressure to restart therapy. Switching from canisterless to canister mode can include turning off the source of negative pressure, removing the dressing, applying appropriate different dressing, selecting a target negative pressure level or setpoint, attaching the canister and connecting the dressing to the canister, and turning on the source of negative pressure to restart therapy. The TNP system can automatically detect which mode it is operating in.

In some cases, the target negative pressure setpoint can be selected only in canister mode. For example, in canister mode, the setpoint can be selected as –60 mmHg, –80 mmHg, –120 mmHg as described herein. The setpoint can be selected using the dial or switch as described herein. In some implementations, additional or alternative setpoint values can be used. In canisterless mode, the setpoint can be preset to a suitable negative pressure, such as –80 mmHg.

Optional carry strap can be attached to the TNP device. For example, the carry strap can be attached through one or more slots in the device housing. Length of the strap can be adjusted as needed. The device can be positioned upright or hung from the strap.

If canister mode is desired, the canister can be installed, for example, by being slid onto the TNP device described herein (which can activate an electromechanical switch configured to indicate canister mode of operation). The dressing can be connected to the canister. For example, the dressing can be connected using a quick-click connector, luer connector, or the like. As described herein, the dressing can be connected to the canister inlet, such as the inlet 161G.

In canisterless mode a dressing can be connected to the TNP device. For example, the dressing can be connected to a connector port of the device, such as the connector port 203G. The dressing can be connected using a luer connector, quick-click connector, or the like.

After the dressing has been properly connected, provision of TNP therapy can be initiated. For example, the user can activate a switch, such as switch 430 illustrated in FIGS. 4A-4B. In some cases, the user can slide the switch, press the switch or the like to activate the negative pressure source. The device can provide an indication that therapy is active, for example, by flashing an indicator 418 illustrated in FIGS. 4A-4B and described herein. The device can provide an indication that the negative pressure setpoint has been reached. For example, the indicator 418 can stop flashing and turn to a solid color as described herein.

At any time, provision of TNP therapy could be paused or stopped. Therapy can be paused by operating the switch as described herein. For example, TNP therapy can be paused to change the canister. The canister may be changed at least once a week or sooner if the canister is full or nearly full. As another example, TNP therapy can be paused to change the dressing when it is full or nearly full. As yet another example, TNP therapy can be paused so that the user can shower.

The canister can be changed or replaced by disconnecting it from the wound dressing and removing the canister, both of which can be performed as described herein. The removed canister can be disposed of and new canister can be installed, as described herein. Dressing can be changed or replaced by removing it, disposing it, and applying a new dressing, as described herein. Provision of therapy can be restarted upon replacement of the canister or dressing as described herein, Power source, such as battery, may need to be periodically recharged. In some cases, the device can indicate via an indicator 412 illustrated in FIGS. 4A-4B that the power source is low or critically low. For example, indicator 412 can turn solid when the power source is low or flash when the power source is critically low. Device can continue to operate while the power source is being charged. Charging can be indicated via an indicator. Completion of charging can be indicated via the indicator.

Various checks of the TNP system may be performed during provision of TNP therapy. Canister or dressing may need to periodically checked and replaced as described herein.

During operation or use, the TNP system can provide various indications to the user. The indications can relate to one or more of power levels, charging, provision of therapy, presence of one or more leaks in a fluid flow path, presence of one or more blockages in the fluid flow path, reaching end of life (for example, 30 days), or the like. The indications can be one or more of visible, such as via one or more LEDs, audible, haptic, tactile, or the like. For example, FIGS. 4A and 4B illustrate various visual indicators on a housing of the pump assembly 150, including 412 (battery level), 414 (blockage), 416 (leak), and 418 (power or provision of therapy) in canisterless (FIG. 4A) and canister (FIG. 4B)

modes of operation. FIG. 4B also illustrates the pump assembly 150 connected to a canister 160.

The illustrated indicators can be configured to provide various indications, such as described herein. Certain indications can be non-critical alarms that do not result in pausing therapy, while certain indications can be critical alarms that result in pausing or stopping therapy. For example, as described herein, detection of a minor or sustainable air leak can be a non-critical alarm that does not result in pausing therapy, whereas detection of a major or unsustainable air leak can be a critical alarm that results in pausing therapy.

Various indications and corresponding user actions can be provided via the indicator 412 as detailed in the following table.

| Appearance | Status | Action |
|---|---|---|
| SOLID AMBER | Low power source. | Charge power source, for example, within 3 hours. |
| FLASHING AMBER | Critically low power source. | Charge power source immediately. |

Various indications and corresponding user actions can be provided via the indicator 414 as detailed in the following table.

| Appearance | Status | Action |
|---|---|---|
| SOLID AMBER | There is a blockage in the system or the cansiter is full and should be replaced. | Therapy is impaired. Troubleshoot blockage/canister full. |
| FLASHING AMBER | Device has detected a blockage over a period of time, such as 1 hour. Therpay has been paused. | Therapy has been interrupted. Troubleshoot blockage/canister full. |

Troubleshooting blockage/canister full can involve one or more of checking the conduit(s) for any kinks, changing the canister, or changing the dressing.

Various indications and corresponding user actions can be provided via the indicator 416 as detailed in the following table.

| Appearance | Status | Action |
|---|---|---|
| SOLID AMBER | There is a leak in the system. | Therapy is impaired. Troubleshoot the leak. |
| FLASHING AMBER | There is a major leak in the system. Therapy has been paused. | Therapy has been interrupted. Troubleshoot the leak. |

Troubleshooting the leak can involve one or more of checking the conduit(s) for any leaks, smoothing out the dressing, or changing the dressing.

Various indications and corresponding user actions can be provided via the indicator 418 as detailed in the following table.

| Appearance | Status | Action |
|---|---|---|
| FLASHING GREEN | Device is opearting to achive the negative pressure setpoint. | Wait unil indicator stops flashing. |
| SOLID GREEN | Therapy is being delivered. | None |
| FLASHING AMBER | Therapy is no longer being delivered | Troubleshoot alarms as described herein. Restart therapy. |
| FLASHING GREEN & AMBER | End-of-life is approaching. Device has a limited period of time, such as 1 day, of therapy remaining. | Obtain a different device if needed. |

Controlling Dual Mode Negative Pressure System

Figure 5:
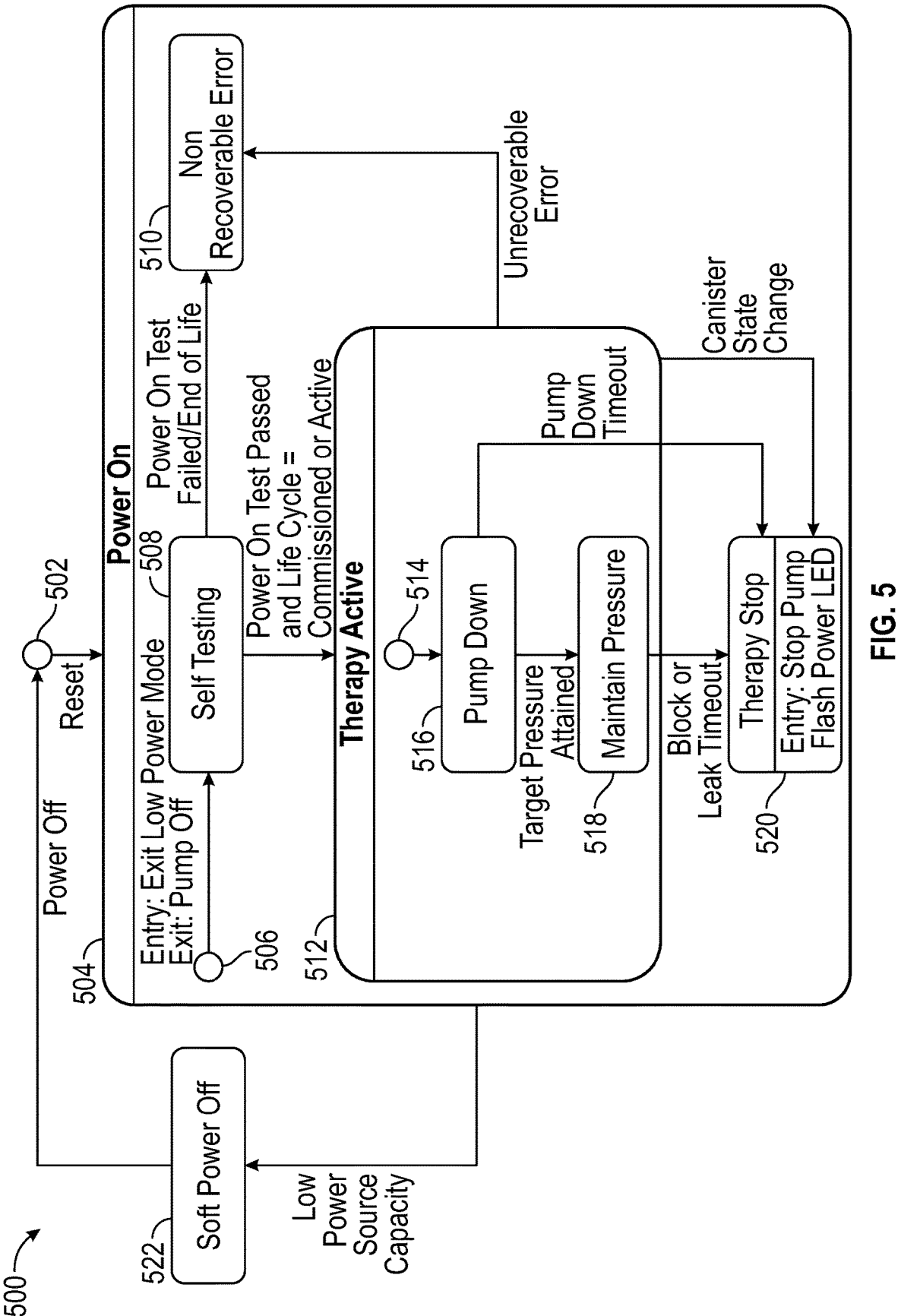
FIG. 5 illustrates a process for controlling the dual mode reduced pressure wound therapy apparatus according to some embodiments.

FIG. 5 illustrates a process 500 for controlling the dual mode reduced pressure wound therapy apparatus according to some embodiments. The process 500, which can also be referred to as a state machine, can be executed by one or more controllers of the TNP system, such as the system 100. The process 500 includes Power Off State 502, Power On States 504, and Soft Power Off State 522. Power On States 504 can include Entry State 506, Self Testing State 508, Non-Recoverable Error (NRE) State 510, Therapy Active States 512, and Therapy Stop State 520. The Therapy Active States 512 can further include Therapy Initialization State 514, Pump Down State 516, and Maintain Pressure State 518.

In some embodiments, operation of the TNP system starts in the Power Off State 502, and the process 500 can transition to the Power On States 504. This transition can be made automatically or in response to a user action, such as in response to a press of an "On" button (for example, one of the buttons 202). The process 500 can transition to the Power On States 504 from Power Off State 502 upon a system reset, which can be performed by the user through one or more of the buttons 202. Such system reset can involve a reset of the one or more controllers.

In some embodiments, the process 500 transitions to the Power On States 504 in response to waking up from the Soft Power Off State 522. In the Soft Power Off State 522, the process 500 can be operating in low power mode, such as by causing the one or more processors to sleep or otherwise consume little power. This transition can be performed automatically, such as after passage of a duration of time. Alternatively or additionally, this transition can be performed in response to a user action as described herein. When the process 500 is in the Soft Power Off State 522, the TNP system may be off and not provide negative pressure.

The process 500 can enter the Power On States 504 via the Entry State 506 as illustrated in FIG. 5. The Power On States 504 can include four sub-states: Self-Testing State 508, Therapy Active States 512, Therapy Stop State 520, and Non-recoverable Error State 510.

Upon transition to the Power On States 504, the process 500 can monitor or continue monitoring power source capacity, such as battery voltage or current. If the power source capacity falls below a certain threshold associated with proper operation of the TNP system, the process can transition to the Soft Power Off State 522. The process 500 can transition from the Power On States 504 to the Soft Power Off State 522 in response to a user action, such as in response to a press of an "Off" button (for example, one of the buttons 202). In some cases, a single button is configured to function as "On" and "Off" button.

Upon entering the Power On States 504, the process 500 can transition into Self-Test State 508. In the Self-Test State 508, the process 500 can perform one or more of power-up self-tests (POSTs) to verify that the TNP system is operating properly. For example, the process 500 can validate memory, verify that the TNP system has not reached end-of-life (EOL) (as explained herein), verify calibration values, or the like. In some cases, validation of memory can utilize Cyclic Redundancy Check (CRC). For example, the process 500 can calculate CRC value on at least a portion of data stored in the memory, compare the calculated CRC value against stored CRC value, and determine if the two CRC values match. This determination can indicate that, for example, firmware of the TNP system 100 is functional and has not been tampered with. This can ensure proper administration of the negative pressure therapy. In some implementations, checking the system's EOL status or calibration profile allows the process 500 to verify that quality of the negative pressure therapy is not compromised. If one or more self-test fails, the process 500 can transition into the Non-Recoverable Error State 510. The Non Recoverable Error State 510 can be a trap state that cannot be left other than by switching off the power (which can cause the transition to the Soft Power Off State 522). The Non Recoverable Error State 510 can also be transitioned into when the process 500 determines that the TNP system has reached EOL from any state.

Upon passing POSTs, the process 500 can transition to the Therapy Active States 512. In some cases, Therapy Active States 512 are entered via the Therapy Initialization State 514. Upon transitioning to the Therapy Active States 512, the process 500 can determine that the TNP system is operating in canister or canisterless mode. For example, as described herein, the process can determine that the switch indicating attachment of a canister has been activated in order to determine that the TNP system is operating in the canister mode.

The process 500 can determine target pressure setpoint depending on the mode of operation. In some cases, in canisterless mode, the target pressure setpoint is preset. For example, the target pressure setpoint in canisterless mode can be −80 mmHg. In some cases, in canisterless mode, the target pressure setpoint can be selected. For example, the target pressure setpoint can be selected using the dial 327G as described herein. For instance, in canister mode, the target pressure setpoint can be selected as −60 mmHg, −80 mmHg, or −120 mmHg. In some cases, the target pressure setpoint can be set once by the process 500 before negative pressure therapy is applied and can remain set until the TNP system has been powered-off and on again.

The process 500 can transition to the Pump Down State 516 in which provision of negative pressure wound therapy is commenced. The process 500 can activate or start the negative pressure source to attempt to reduce pressure at the wound to the target pressure setpoint. The process 500 can monitor pressure at the wound with one or more pressure sensors positioned in a fluid flow path connecting the negative pressure source to the dressing. When the pressure has been successfully reduced to the target set point, the process 500 can transition to the Maintain Pressure State 518. In some cases, the process 500 can stop or deactivate the source of negative pressure when the target set point has been reached or attained. In some cases, the process 500 can slow down the source of negative pressure when the target set point has been reached or attained.

In the Maintain Pressure State 518, the target pressure can be maintained, for example, by activating the negative pressure source pump when pressure at the wound has decreased above the target pressure setpoint and deactivating the negative pressure source when the target pressure has been restored. Pressure at the wound can decrease above the setpoint (or become more positive) due to one or more leaks in the fluid flow path.

In both Pump Down State 516 and Maintain Pressure State 518, various system parameters, such as pressure at the wound, level of activity of the negative pressure source, or the like, can be monitored to determine whether negative pressure wound therapy should be stopped or additional or alternative indication should be provided. Such additional or alternative indication can include the process 500 providing one or more of visual (such as, using one or more indicators 204), audible, haptic, tactile, or the like indications. Such determination can be based on finding of one or more blockages or leaks in the fluid flow path. In some cases, level of activity of the negative pressure source can be monitored via determining duty cycle of the negative pressure source, which can reflect proportion of time the negative pressure source is active over a time duration. In some embodiments, as explained herein, a timeout mechanism (such as, monitoring the blockage or the leak duration) or determination scheme using a hysteresis can be used to reduce a likelihood of false positives in the blockage or the leak detection.

In some cases, detection of a leak or blockage can cause the process 500 to transition into the Therapy Stop State 520 from one or more of Pump Down 516 or Maintain Pressure 518 States. In this state, negative pressure source can be stopped to pause provision of therapy. The process 500 can transition to the Therapy Stop State 520 in response to detecting: (1) pump down time indicative of a leak in canister or canisterless mode, (2) timeout indicative of blockage while maintaining pressure in the canister mode, (3) timeout indicative of a leak while maintaining pressure in canister or canisterless mode, or the like.

In some embodiments, the process 500 can distinguish between sustainable and unsustainable leaks or blockages as described herein. For example, a sustainable leak or blockage can be associated with less intense condition(s) that do not necessitate pausing or stopping therapy. Rather, the process 500 can indicate presence of the sustainable leak or blockage as described herein to permit the user to remedy the leak or blockage without the necessity to interrupt therapy. As another example, an unsustainable leak or blockage can be associated with more intense condition(s) that necessitate pausing or stopping therapy. Such unsustainable conditions can be so severe that continuing operation of the negative pressure source to provide therapy can drain the capacity of the power source.

In some implementations, when the target pressure setpoint cannot be reached in the Pump Down State 516 over a duration of time, the process 500 can determine presence of a leak. The process 500 can determine that such leak that prevents reaching the setpoint is unsustainable and indicate its presence by stopping the negative pressure source. Additionally, the process 500 can indicate presence of the unsustainable leak visually, audibly, haptically, tactilely, or the like as described herein. Unsustainable leaks can be due to, for example, disconnecting the dressing from the negative pressure source when operating in the canisterless mode or disconnecting the canister when operating in the canister mode.

In some embodiments, the process 500 may not be able to restore the target pressure at the wound in the Maintain Pressure State 518 due to presence of a leak or blockage in the fluid flow path. The process 500 can distinguish between leak or blockage by comparing the level of activity of the negative pressure source, such as the duty cycle, to a leak threshold or blockage threshold as described herein. When blockage is present, fluid flow path volume through which the negative pressure source moves fluid is reduced. As a result, the level of activity of the negative pressure source decreases. When leak is present, fluid flow path volume through which the negative pressure source moves fluid is increased. As a result, the level of activity of the negative pressure source increases. By using different leak and blockage thresholds, the process 500 can distinguish between leak and blockage conditions. Leak and blockage thresholds can be selected or adjusted to account for canister or canisterless modes of operation. This can be advantageous because of different fluid flow path volumes when operating in both modes. For example, the fluid flow path volumes when operating in canister mode includes additional volume of the canister, which is not present in the canisterless mode.

In some implementations, the process 500 monitors lifetime or usage time of the TNP system. For example, the process 500 can only update the lifetime in the Therapy Active States 512. Lifetime can be measured as total amount of time the negative pressure source has been active since initial activation of the TNP system. In some implementations, the process 500 can start measuring or monitoring lifetime only after a therapy has been successfully provided for a threshold period of time, such as 1 minute, 5 minutes, 10 minutes, 20 minutes, 25 minutes or the like. Successfully provision of therapy can correspond to being able to attain and maintain target pressure.

The process 500 can monitor the lifetime to determine when it the TNP system reaches end of life, such as 7 days of operation, 10 days of operation, 30 days of operation, or like. The process 500 can determine when the TNP system has reached or exceeded its expected therapy operation life or EOL. When the process 500 detects that EOL has been reached, ability of provide negative pressure wound therapy is disabled. One or more of visual, audible, haptic, tactile, or the like indications can be provided as described herein. In some cases, upon detecting EOL, the process 500 transitions to the Non-Recoverable Error State 510, in which provision of therapy is disabled.

In some implementations, the process 500 can perform an EOL check by using or maintaining Real-Time Clock (RTC) and accumulated usage time. The accumulated usage time may be stored in persistent memory, such as an EEPROM. The process 500 can periodically update the accumulated usage time using RTC. For example, for every 15 minutes as determined by RTC, the process 500 can add 15 minutes to the accumulated usage time.

The process 500 can perform EOL check in the Self Testing State 508 when starting or restarting therapy or periodically. In some embodiments, the EOL check may be performed upon a request by the processor in the Soft-Power Off State 522. The request will trigger the EOL check asynchronously instead of waiting for a periodic EOL check event, and immediately transition the system into Non-Recoverable Error State 510 in response to determining that EOL has been reached As described herein, the process 500 can determine and indicate presence of one or more blockages or leaks in the fluid flow path. In some embodiments, the process 500 can make such determination from pressure in the fluid flow path and level of activity of the negative pressure source. Level of activity can, for example, be determined by monitoring a duty cycle of the negative pressure source, which is associated with a proportion of time the negative pressure source is active over a time duration. For example, if the negative pressure source is active for 50 seconds over a duration of one minute, the process 500 can determine that the duty cycle is 0.83 (50/60) or 83% (50/60*100%).

In some implementations, the duty cycle can be used to determine presence of a blockage or leak. Generally, the negative pressure source should not work too hard or too little, which can respectively translate directly to high pump or low duty cycle. When the negative pressure source is working too hard (corresponding to a high duty), a presence of a leak can be suspected as the negative pressure source is working extra hard to move more fluid than expected to attempt to reach the target pressure setpoint. When the negative pressure source is working too little, a presence of a blockage can be suspected as the negative pressure source not working hard enough because is moves less fluid than expected to attempt to reach the target pressure setpoint. Thus, the process 500 can use one or more pump duty cycle thresholds for comparison with the calculated pump duty cycles to determine whether the one or more thresholds have been satisfied and indicate a blockage or leak.

Figure 6A:
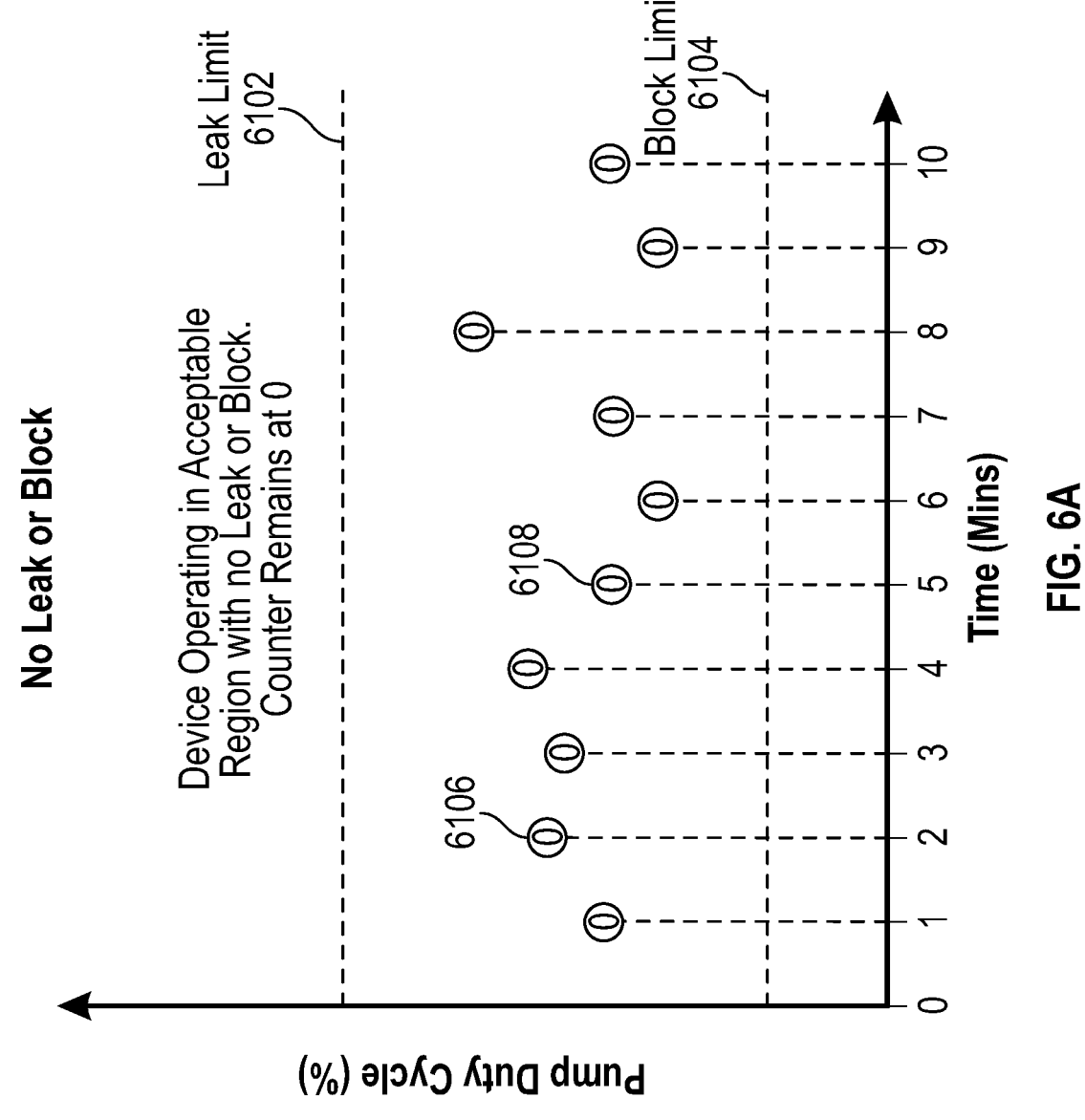
FIGS. 6A-6D illustrate detection and indication of a leak or blockage condition according to some embodiments.

FIG. 6A is a diagram 6100 illustrating normal operation of a TNP system, such as the system 100, according to some embodiments. On the y-axis is the negative pressure source, for example a pump, duty cycle. On the x-axis is time denominated in minutes. The measured or calculated pump duty cycles (such as, 6106 and 6108) are plotted according to their values. Along the Y-axis, a leak threshold 6102 and a blockage limit threshold 6104 are presented. A leak condition can be detected when the pump is working harder than expected or desired, thus exceeding the leak threshold 6102. Conversely, a blockage condition can be detected when the pump is working too little to maintain the target pressure setpoint, thus falling below the blockage threshold 6104. Leak or blockage thresholds can be different depending on canister or canisterless mode of operation. For example, the leak threshold can be higher in canister mode than in canisterless mode, such as 12% and 4% respectively. This can be due to the TNP system being expected to move more fluid in the canister mode. In some embodiments, the process 500 can detect blockage and leak conditions in the canister mode, but only the leak condition in the canisterless mode.

In FIG. 6A, as none of the pump duty cycles are above the threshold 6102 or below the threshold 6104, the TNP system is operating normally. The process 500 can remain in the Therapy Active States 512.

In some embodiments, the process 500 can implement hysteresis when detecting blockage or leak. This can be performed to reduce the risk of a false positive determination, which can lead to an incorrect transition to the Therapy Stop State 520. Such false positive determination could be due to a temporary leak or blockage.

Figure 6B:
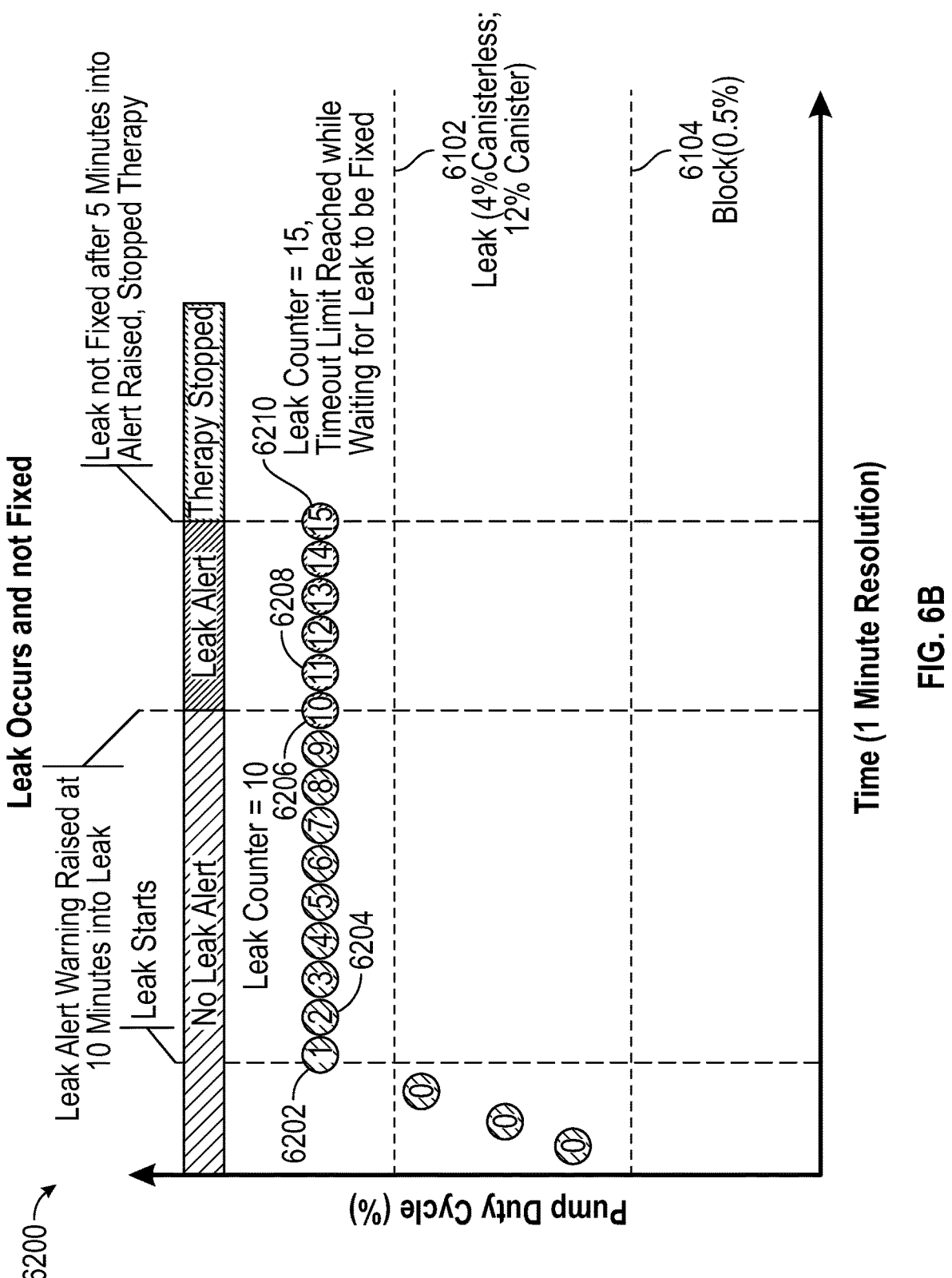

FIG. 6B is a diagram 6200 illustrating detection and indication of a leak condition according to some embodiments. As illustrated, the pump duty cycles are continuously increasing and start to exceed the leak threshold 6102. When the pump duty cycle exceeds the leak limit threshold 6202, the process 500 can, instead of immediately providing indication of a leak, implement hysteresis. For example, after the initial duty cycle 6202 above the leak threshold 6102, the process 500 tracks the next pump duty cycle reading 6204 to determine that it also exceeds the threshold 6102. The process 500 can keep track of pump duty cycle readings that exceed the threshold 6102 (the count of such pump duty cycle readings exceeding the threshold 6102 is shown in the diagram 6200, for example, "2" is embedded in the second pump duty cycle reading 6204). The process 500 can keep a counter that is incremented with each consecutive or non-consecutive duty cycle reading exceeding the threshold 6102. The process 500 can indicate presence of a leak when the counter reaches a threshold, such as 10 as illustrated in FIG. 6B with the pump duty cycle 6206. As is shown, consecutive pump duty cycles were counted over a 10 minute interval.

The process 500 can provide a leak indication, alarm, or alert when the threshold is reached with the pump duty cycle 6206. As described herein, such alert can include one or more of visual, audible, tactile, haptic or the like alerts. The alert can provide an indication to the user to address the leak before stopping the therapy. For example, the process can provide a duration of time to address the leak. During this time, the process 500 can continue to increment the counter for each pump duty cycle sample indicative of the leak condition. For example, FIG. 6B illustrates that the pump duty cycle 6208 counts it as 11th pump duty cycle exceeding the leak threshold 6102. The duration of time for the user to address the leak can be shorter than the duration of time for detecting the leak. For example, the respective durations illustrated in FIG. 6B are 10 minutes for detecting the leak and 5 minutes for addressing the leak.

When the process 500 determines that the leak condition has persisted beyond the duration for addressing the leak, the process 500 can stop provision of negative therapy. This can be performed to mitigate reduction of capacity of the power source, minimizing user discomfort (for example, due to noise from operating the negative pressure source), or the like. The process 500 can transition to the Therapy Stop State 520. As shown in FIG. 6B, the process 500 can stop therapy after determining that the duty cycle 6210 exceeds the leak threshold 6102. The process 500 can continue providing the same or provide different indication or alert when therapy has been stopped.

In some embodiments, a measured pump duty cycle may greatly exceed the leak threshold 6102. For example, when one or more pump duty cycles are at or approximately 100% for a duration of time, this may indicate a catastrophic leak where the pump is working to its fullest but cannot attain the target pressure. Such catastrophic leaks are unsustainable and can compromise the effectiveness of a therapy or rapidly drain the power source. For example, catastrophic leaks can occur as a result of a removed dressing in canisterless mode, removed canister in canister mode (which can be detected via the switch), or disconnecting the negative pressure source from the fluid flow path in either mode. In these scenarios, while the pump may work strenuously (such as, near 100% pump duty cycle) to try to achieve the target pressure setpoint, but may not be able to do so. As further described herein, the process 500 can detect catastrophic leak by determining that the pump operates at or near 100% duty cycle over a time duration and, in response to the detection, stop provision of negative pressure. The process 500 can provide an alert as described herein.

Figure 6C:
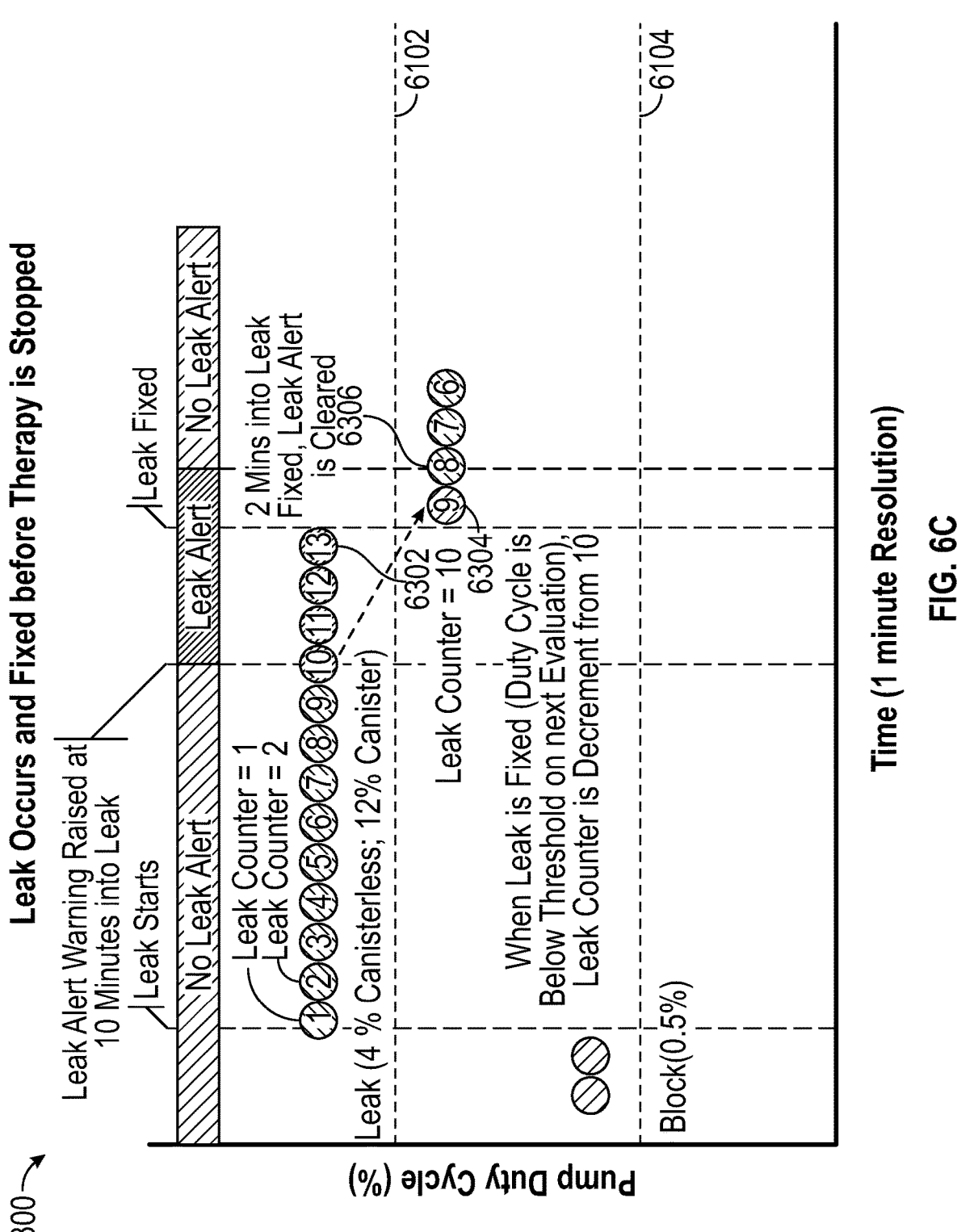

FIG. 6C is a diagram 6300 illustrating detection of a leak condition according to some embodiments. Here, unlike FIG. 6B, the leak condition is fixed after the initial detection (for example, within 5 minutes). As shown, after the 13th count caused by the pump duty cycle 6302 exceeding the leak threshold 6102, the next pump duty cycle 6304 is below the threshold 6102 due to the leak being fixed. The fix may have occurred in the minutes prior and the pump may have taken some time to bring the pressure down enough such that the pump duty cycle 6304 is below the leak threshold 6102.

The process 500 can implement hysteresis with clearing the detection or indication of leak. This can be performed to prevent false negatives. Upon detecting that the duty cycle is below the threshold 6102, the process 500 can decrement the counter. As illustrated, because counter of 10 directs the process 500 to initiate the leak alert, the process can decrement the counter to 9. If the subsequent pump duty cycle 6306 remains below the leak threshold 6102, the process 500 can clear detection or indication of the leak. The process 500 can decrement the counter to 8. The duration of time for clearing the leak can be shorter than the duration of time for detecting the leak. For example, the respective durations illustrated in FIG. 6C are 10 minutes for detecting the leak and 2 minutes for clearing the leak.

Figure 6D:
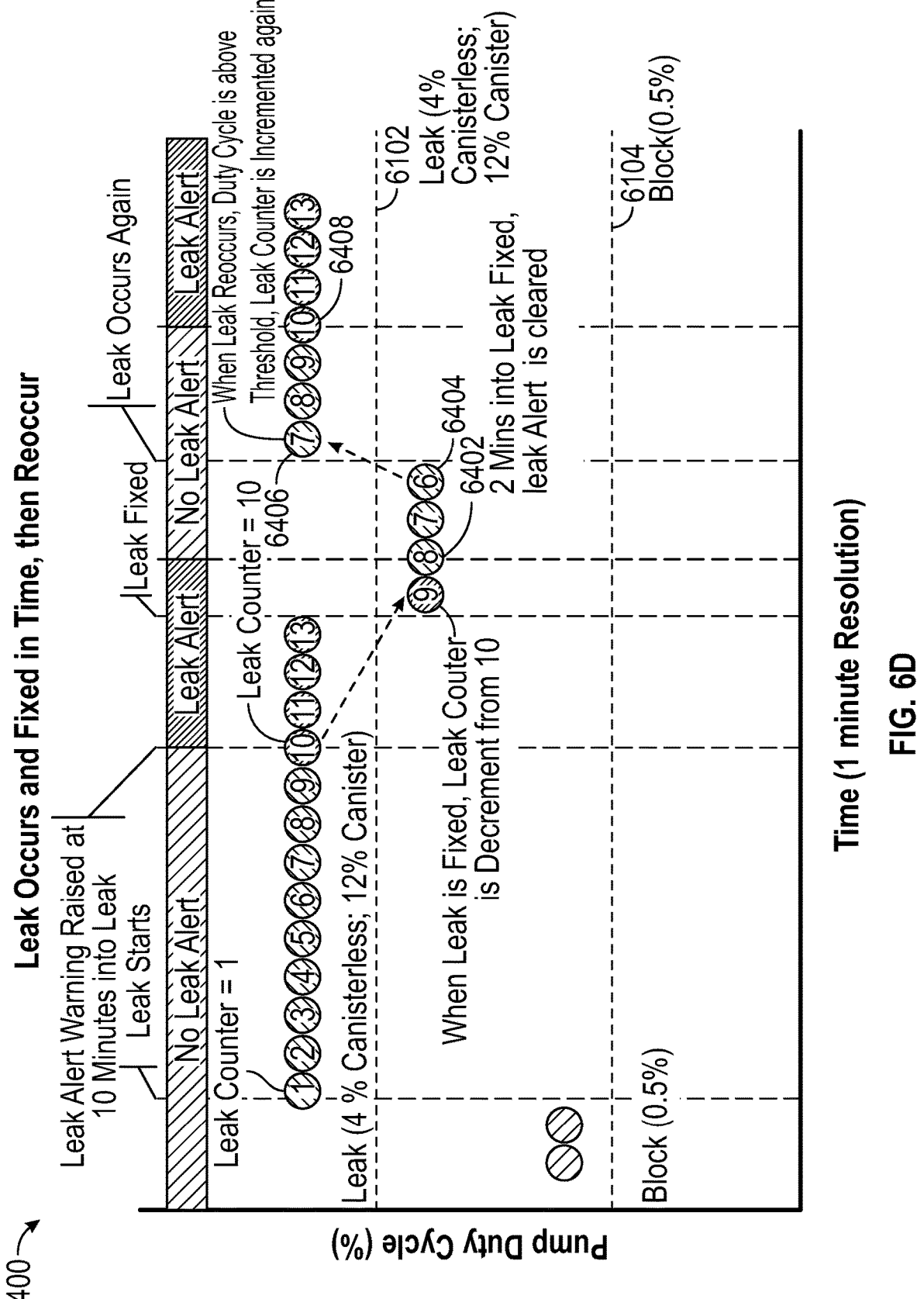

FIG. 6D is a diagram 6400 illustrating re-detection of a leak condition according to some embodiments. In contrast with FIG. 6C, the leak condition re-occurs in FIG. 6D. After leak is cleared with the pump duty cycle 6402 being below the leak threshold 6102, the process 500 can continue to monitor for a recurrence of a leak condition with knowledge of the history of prior pump duty cycles. For example, the counter could be reset to 8 on the duty cycle 6402 as explained herein. Subsequent detection of the pump duty cycles below the threshold 6102 can cause the counter to be decremented further, for example, to 7 and 6 with the pump duty cycle 6404. Such decrementing can continue until the leak counter reaches a number indicative of a normal operating condition, such as 0.

However, if a subsequent measured pump duty cycle, such as the duty cycle 6406, reverts back to indicating a leak condition (for example, exceeds the leak threshold 6102), the process 500 can increment the leak counter 6406 again. As explained in connection with FIG. 6B, when the counter reaches the threshold (such as, 10), the process 500 can reassert the leak indication. As is illustrated, this can occur when the process 500 detects that the pump duty cycle 6408 exceeds the leak threshold 6102.

In some embodiments, the approach of FIGS. 6A-6D is advantageous as it provides, based on the history of the leak condition detections, a more responsive leak detection, while also allowing for one or several duty cycles to be above the leak limit threshold 6102 without triggering the leak indication. A user attending to the leak indication can more readily and quickly determine whether the fix provided a lasting fix. For example, the user may have fixed a visible leak to remove the leak indication, but the process 500 can detect other leaks that cause reassertion of the leak indication.

Although FIGS. 6A-6D illustrate leak detection, blockage detection can be similarly performed using the blockage threshold 6104. The process 500 can detect pump duty cycles falling below the threshold 6104.

Figure 7:
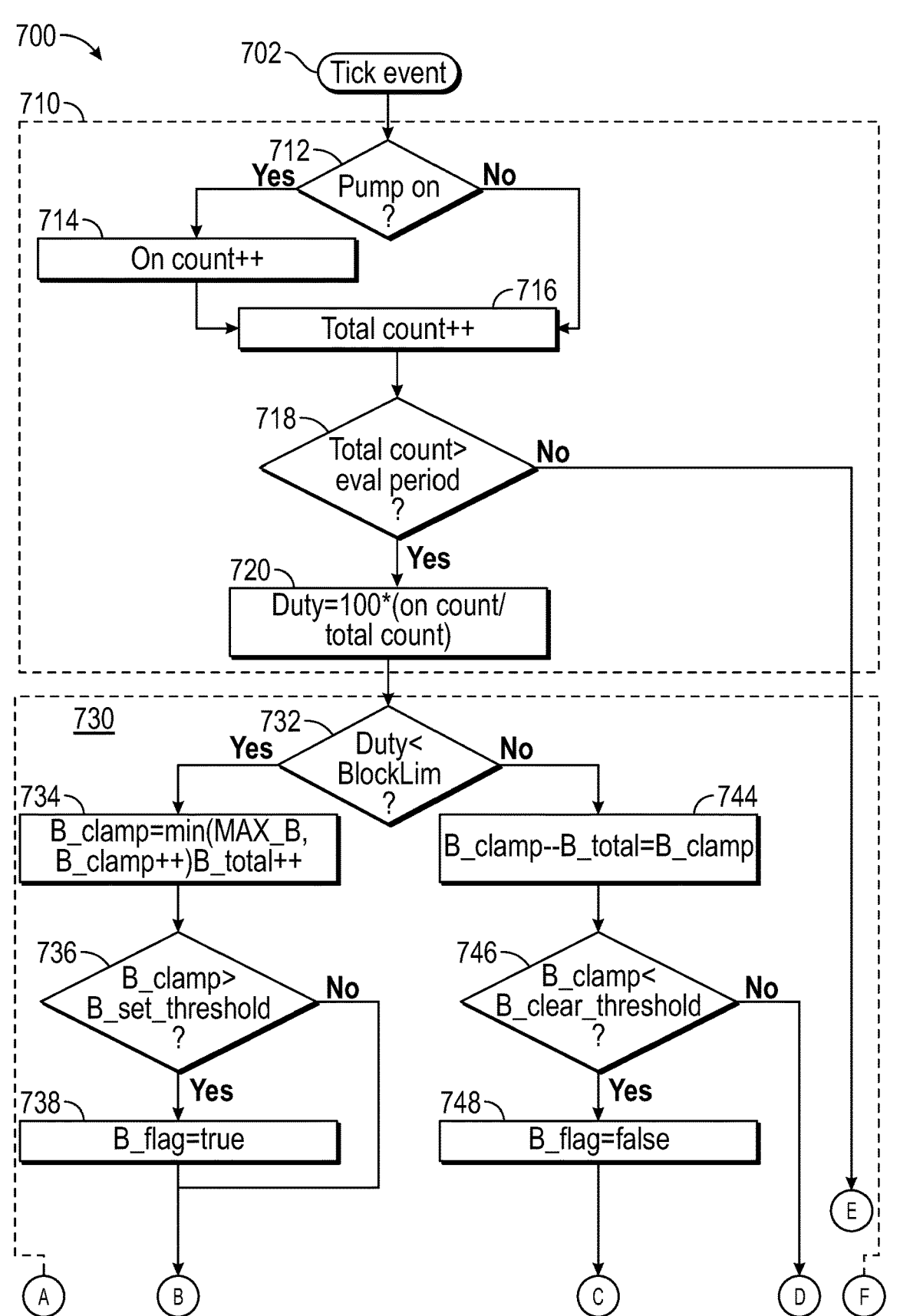
FIG. 7 illustrates a flowchart of blockage and leak detection and indication according to some embodiments.
Figure 7:
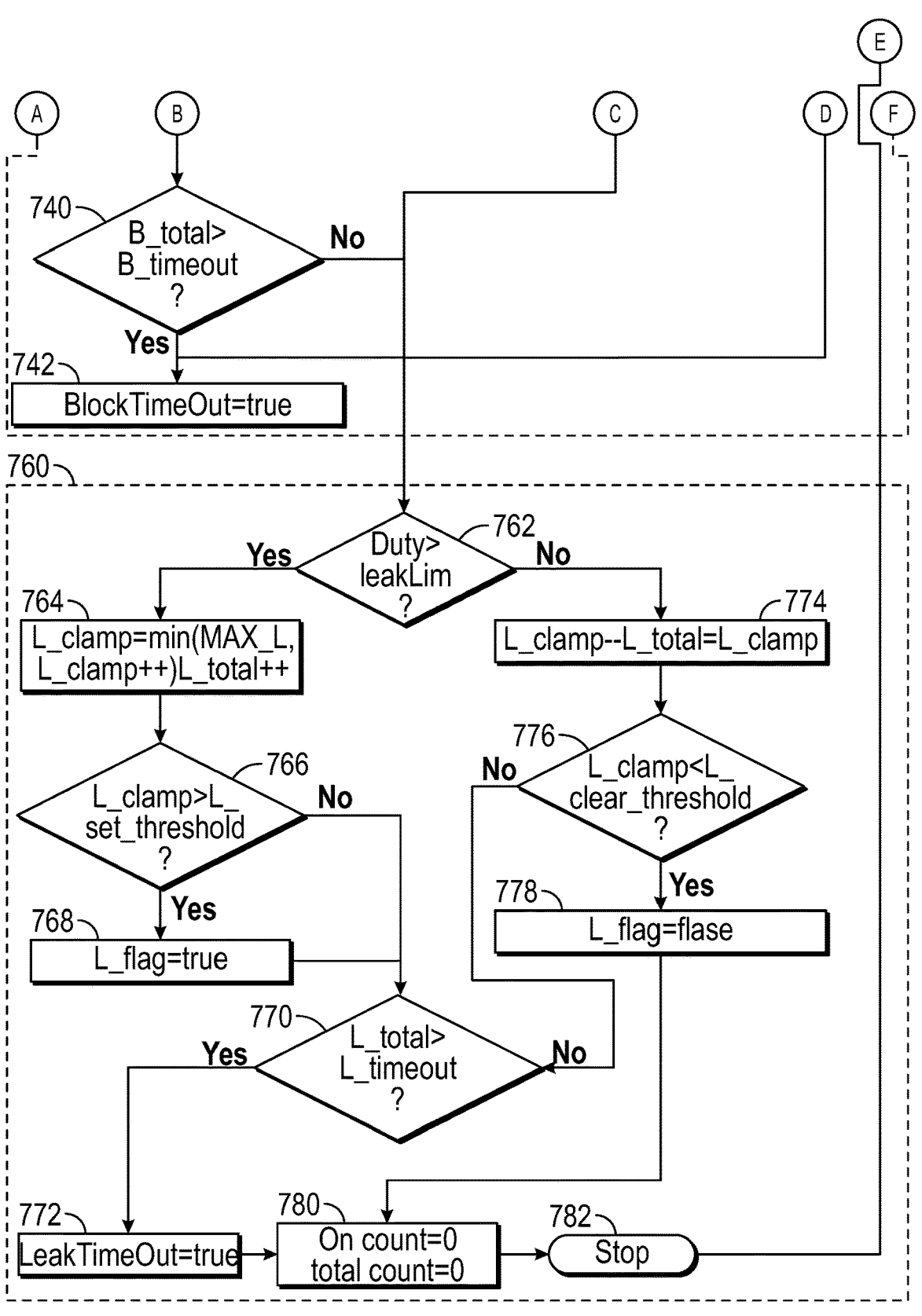

FIG. 7 illustrates a flowchart 700 of blockage and leak detection and indication according to some embodiments. The process 700 can be executed by one or more controllers of the TNP system, such as the system 100. The process 700 can be executed periodically, such as when a scheduled tick event 702 occurs, to monitor an occurrence of a blockage or leak condition. While the flowchart 700 provides all three aspects of the implementation in a single flowchart, including the calculation of activity 710 (illustrated as pump duty cycle), blockage detection 730, and leak detection 760, one or more of these can be independently implemented in a separate flow chart.

At block 702, the process 700 detects a system tick event 702. The tick event 702 can be based on one or more interrupts, clocks, or the like. The process 700 can address the tick event 702 by calling upon associated functions interrupt handlers or functions, which can include the pump duty cycle calculation 710.

The pump duty cycle calculation 710 can include blocks 712, 714, 716, 718, and 720. At block 712, the process 700 can determine whether the negative pressure source or pump is active or not. If the pump is determined to be in the active state, the process 700 can increment a pump activity counter (for example, "onCount") in block 714. Otherwise, the pump activity counter is not incremented.

In block 716, time duration is updated, such as incremented for each observed tick event. In some embodiments, the process 700 can delay calculating the duty cycle until the time duration reaches a threshold (for example, "evalPeriod"), such as 1 minute. For example, assuming 10 millisecond tick with 1 minute threshold, the process 700 can determine that the threshold has been reached with 6,000 or more counts (10 milliseconds*100*60 seconds=1 minute). In block 718, the process 700 can compare the time duration against the threshold. If it is determined that the threshold has been reached, the process 700 can update the pump duty cycle in block 720 as proportion of the pump activity counter (block 714) to the time duration (block 716) expressed as a percentage. Otherwise, the process 700 can determine that it is too early to perform the detection and transition to block 782 to end the process.

The process 700 can use the pump duty cycle determined in bloc 720 to detect or indicate a blockage or a leak in 730 or 760, respectively. Although FIG. 7 illustrates first performing the blockage detection 730 followed by the leak detection 760, in some embodiments leak detection can precede blockage detection.

Blockage detection 730 can include blocks 732, 734, 736, 738, 740, 742, 744, 746, and 748). In block 732, it can be determined if the pump duty cycle is below the blockage threshold (see, for example, 6104 in FIGS. 6A-6D). For example, in the canister mode the blockage threshold can be 0.5% duty cycle. If the process 700 determines that the pump duty cycle is below the blockage threshold, the process transition to block 734, where it can increment a blockage counter (for example, "B_total") and blockage hysteresis counter (for example, "B_clamp"). The blockage hysteresis counter can have a ceiling value (for example, "MAX_B") associated with blockage alert as described herein. For example, with reference to FIGS. 6A-6D, a blockage detection duration is 10 minutes. If the process 700 executes blockage detection 730 every minute, the blockage hysteresis counter can be set to 10. At block 734, both counters can increase up to 10 for each execution of blockage detection 730, but from 10, only the blockage counter can increase to 11 or beyond.

The process 700 can transition to block 736, where it can compare the blockage hysteresis counter against a blockage threshold counter (for example, "B_set_threshold") to determine whether a blockage condition has persisted long enough to activate blockage alert. If the blockage hysteresis counter exceeds blockage duration, sufficiently long time (for example, more than 10 minutes as in FIG. 6B) has passed with the pump duty cycle being below the blockage threshold. Blockage alert can be activated as described herein. The process 700 can transition to block 738 where it can set blockage alert (for example, "B_Flag") to true.

The process 700 can transition to block 740, where the blockage counter can be compared against a blockage threshold associated with stopping therapy (for example, "B_timeout"). This determination can be made to assess whether to stop the therapy because of the persisting blockage condition. With reference to FIG. 6B, such blockage threshold can be 5 minutes for addressing the blockage. If the comparison in block 740 is true, the process 700 can transition to block 742 where it can indicate that therapy should be stopped (for example, by setting "BlockTimeOut" to true). In some cases, the process 500 can transition the system into Therapy Stop State 520.

In block 732, if the process 700 determines that the pump duty cycle exceeds the blockage limit threshold (for example, 6104), the process 700 can transition to block 744. In block 744, the process 700 can decrement the blockage hysteresis counter (for example, "B_clamp") and reset the block counter (for example, "B_total") to the block hysteresis counter. As described herein, the blockage hysteresis counter can be associated with a ceiling value (for example, "MAX_B"). Decrementing the blockage hysteresis counter can result in a value less than the ceiling value. For example, with reference to FIG. 6C, after the detection of a normal pump duty cycle, the leak counter is reset to 9 (for example, 10 decremented by 1). Similarly, the blockage counter can be reset to 9.

The process 700 can transition to block 746, wherein blockage hysteresis counter can be compared against a blockage clear threshold (for example, "B_clear_threshold") to determine whether to clear the blockage alert. The process 700 can require certain number of normal pump duty cycles before clearing. For example, FIG. 6C illustrates at least 2 counts of normal duty cycle before clearing the leak alert. Similarly, the process 700 can set the blockage hysteresis counter to 8. For example, decrementing block hysteresis counter of 10 will take two minutes before clearing the blockage alert in block 748. While a floor for the blockage hysteresis counter (for example, "B_clamp") is not illustrated in FIG. 7, in some embodiments, such floor can be used in order to not decrease the blockage hysteresis counter indefinitely.

In some embodiments, leak detection can be performed similarly to blockage detection except that the process 700 can determine if the pump duty cycle exceeds a leak threshold. Leak detection 760 can include blocks 762, 764, 766, 768, 770, 772, 774, 776, and 778. In block 762, the process 700 can determine if the pump duty cycle determined in block 720 is above the leak threshold (for example, 6102 in FIGS. 6A-6D). For example, in the canister mode, leak threshold of 12% can be used, and in canisterless mode, leak threshold of 4% can be used. If the process 700 determines that the pump duty cycle is above the leak threshold, the process 700 can transition to block 764. The process 700 can increment a leak counter (for example, "L_total") and a leak hysteresis counter (for example, "L_clamp"). The leak hysteresis counter can have a ceiling value (for example, "MAX_L") associated with leak alert as described herein.

The process can transition to block 766, where it can compare the leak hysteresis counter against a leak threshold count (for example, "L_set_threshold") to determine whether a leak condition has persisted long enough to active a leak alert. If the leak hysteresis counter exceeds leak duration, sufficiently long time (for example, 10 minutes in FIG. 6B) has passed with the pump duty cycle being above the leak threshold. Leak alert can be activated as described herein. The process can transition to block 768 where it can set blockage alert (for example, "L_Flag") to true.

The process 700 can transition to block 770, where the leak counter can be compared against a leak threshold associated with stopping therapy (for example, "L_timeout"). This determination can be made to assess whether to stop the therapy because of the persisting leak condition. With reference to FIG. 6B, such leak threshold can be 5 minutes for addressing the leak. If the comparison in block 770 is true, the process 700 can transition to block 772 where it can indicate that therapy should be stopped (for example, by setting "LeakTimeOut" to true). In some cases, the process 500 can transition the system into Therapy Stop State 520.

In block 762, if the process 700 determines that the pump duty does not exceed the leak threshold, such as 6102, the process 700 can transition to block 774. In block 744, the process 700 can decrement the leak hysteresis counter (for example, "L_clamp") and reset the leak counter (for example, "L_total") to the leak hysteresis counter. As described herein, the leak hysteresis counter can be associated with a ceiling value (for example, "MAX_L"). Decrementing the leak hysteresis counter can result in a value less than the ceiling value. For example, with reference to FIG. 6C, after the detection of a normal pump duty cycle, the leak counter is reset to 9 (for example, 10 decremented by 1).

The process can transition to block 776, wherein leak hysteresis counter can be compared against a leak clear threshold count (for example, "L_clear_threshold") to determine whether to clear the leak alert. The process 700 can require certain number of normal pump duty cycles before clearing. For example, FIG. 6C illustrates at least 2 counts of normal duty cycle before clearing the leak alert. Similarly, the process 700 can set the leak hysteresis counter to 8. For example, decrementing leak hysteresis counter of 10 will take two minutes before clearing the leak alert in block 778. While a floor for the leak hysteresis counter (for example, "L_clamp") is not illustrated in FIG. 7, in some embodiments, such floor can be used in order to not decrease the leak hysteresis counter indefinitely.

In some embodiments, the process 700 can reset the pump activity counter (for example, "onCount") and the time duration (for example, "totalCount") in block 780 before terminating. This can allows the pump duty cycle calculation 710 to start with a clean set of variables for calculation of the next pump duty cycle.

While illustrated leak detection 760 does not distinguish between a sustainable leak and an unsustainable leak, in some embodiments, the process 700 can make such distinction. For example, leak detection 760 can use a higher leak threshold (such as, at or close to 100% ad described herein) for the detection of unsustainable leak.

Escalation of Alerts

FIGS. 8A and 8B illustrate escalation of blockage and leak alerts according to some embodiments. FIG. 8A illustrates escalation of leak alert in canister mode and canister-less mode (or canister-free mode). FIG. 8B illustrates escalation of a blockage alert in canister mode.

As described, a TNP system, such as the system 100, can detect a sustainable leak 8102 or an unsustainable leak 8106 or 8108. This detection can be performed by the process 500. For a sustainable leak, a target pressure setpoint is attainable. In some cases, when at least some pump duty cycles exceed the leak threshold, such as the threshold 6102, leak can be detected as described herein. Such sustainable leak may occur as a result of a wound dressing that is not fully sealed.

In some embodiments, as described herein, when sustainable leak is detected, the therapy may not have been fully compromised, and patient may gain at least some benefits from continuing provision of therapy. The TNP system 100 or process 500 can provide a minor leak alert 8104 to bring the leak to user's attention, but continue to deliver negative pressure wound therapy. As illustrated, minor leak alert 8104 can include providing one or more of a visual indication or an audio alert. As described herein, visual indication can be provided via a leak indicator 8112 (which can correspond to the indicator 416). For example, the indicator can be turned amber. Audio indication can be provided by activating a buzzer. Additional or alternative indications can be provided as described herein.

In some implementations, over time, what started out as a sustainable leak may deteriorate into an unsustainable leak 8106. For example, a small air leak due to a wound dressing that is not fully sealed may continue to get larger over time. Eventually, the negative pressure source may be operating at or near its full capacity to attempt to maintain the target pressure setpoint. As described herein, this can be detected from the pump duty cycle being at or near 100%. When it is determined that the negative pressure source cannot achieve or maintain the target pressure setpoint, it can be determined that therapy has been compromised by the leak and the patient is no longer receiving benefits from the therapy.

When a sustainable leak develops into an unsustainable leak, previous minor leak alert 8104 can be escalated to a major leak 8110. The TNP system 100 or process 500 can continue to alert the user, but turn off the negative pressure source. In some cases, major leak alert 8110 uses different indicators or different combination of indicators than the minor leak alert 8106 to distinguish the greater severity of the leak condition. As described herein, for example, the leak indicator 8112 (which can correspond to the indicator 416) can be amber and the on/off indicator 8114 (which can correspond to the indicator 418) can be green, respectively, for provision of the minor leak alert 8104, while both indicators can be amber for provision of the major leak alert 8110. Audio alert can also be provided. Additional or alternative indications can be provided as described herein.

In some embodiments, an unsustainable leak can be detected directly without first detecting the minor leak alert. For example, this can occur when the TNP system 100 is unable to achieve the target pressure setpoint in the Pump Down State 516. The cause can be operating in the canister mode without canister attached or operating in canisterless mode without wound dressing attached. In such situations, the TNP system 100 or process 500 can stop the therapy and provide the major leak alert 8110 without first providing the minor leak alert 8104.

FIG. 8B illustrates escalation of a blockage alert in canister mode. Although not illustrated, the flow illustrated in FIG. 8B can be performed in canisterless mode. In block 8202, the TNP system 100 or process 500 can detect blockage as described herein. For example, when at least some pump duty cycles do not meet the blockage threshold, such as the threshold 6104, blockage can be detected as described herein. Blockage can be caused by a full or substantially full canister or blockage in the fluid flow path.

In some embodiments, when blockage is detected, a minor blockage alert 8204 is provided. The TNP system can continue delivery of negative pressure wound therapy as the patient may be receiving at least some benefits. As illustrated, minor blockage alert 8204 can include providing one or more of a visual indication or an audio alert. As described herein, visual indication can be provided via a blockage indicator 8210 (which can correspond to the indicator 414). For example, the indicator can be turned amber. Audio indication can be provided by activating a buzzer. Additional or alternatives indication can be provided as described herein.

The TNP system 100 or process 500 can continue to monitor the blockage, for example via monitoring the duration of blockage. When it is determined that blockage is persistent 8206 (for example, lasts over an hour), it is likely that a patient is not gaining any benefits from provision of therapy.

When persistent blockage 8206 has been determined, in some embodiments, the TNP system or process 500 can escalate the blockage alert from the minor blockage alert 8204 to a major blockage alert 8208. In some implementations, provision of therapy can be stopped. In some cases, major blockage alert 8208 uses different indicators or different combination of indicators than the minor blockage alert 8204 to distinguish the greater severity of the blockage condition. For example, the blockage indicator 8210 (which can correspond to the indicator 414) can be amber and the on/off indicator 8212 (which can correspond to the indicator 418) can be green, respectively, for provision of the minor blockage alert 8204, while both indicators can be amber for provision of the major blockage alert 8208. Audio alert can also be provided. Additional or alternative indications can be provided as described herein.

Other Variations

Control systems and methods disclosed herein can be implemented by any TNP system or any medical device. As used herein, stopping therapy encompasses suspending or pausing therapy. While certain colors of indicators may be described in connection with various examples, any suitable color can be additionally or alternatively used. Although this disclosure describes certain embodiments, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. Indeed, a wide variety of designs and approaches are possible and are within the scope of this disclosure. No feature, structure, or step disclosed herein is essential or indispensable. Moreover, while illustrative embodiments have been described herein, the scope of any and all embodiments having equivalent elements, modifications, omissions, combinations (for example, of aspects across various embodiments), substitutions, adaptations and/or alterations as would be appreciated by those in the art based on the present disclosure. While certain embodiments have been described, these embodiments have been presented by way of example only, and are not intended to limit the scope of protection.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures may be implemented as software and/or firmware on a processor, controller, ASIC, FPGA, and/or dedicated hardware. Hardware components, such as processors, ASICs, FPGAs, and the like, can include logic circuitry.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A negative pressure wound therapy apparatus comprising:

a negative pressure source configured to provide negative pressure via a fluid flow path to a wound covered by a wound dressing; and a controller configured to operate the negative pressure source to provide negative pressure to the wound, the controller further configured to:

monitor for an occurrence of a leak condition in the fluid flow path or a blockage condition in the fluid flow path during a time period of a plurality of time periods during which the negative pressure source provides negative pressure to the wound;

increment a counter responsive to detecting the occurrence of the leak condition in the fluid flow path or the blockage condition in the fluid flow path during the time period;

responsive to not detecting the occurrence of the leak condition in the fluid flow path or the blockage condition in the fluid flow path during the time period:

decrement the counter to a value that is greater than zero if the counter has a value greater than one, and decrement the counter to a value of zero if the counter has a value of one;

responsive to the counter satisfying a first threshold, provide a first indication of the occurrence of the leak condition in the fluid flow path or the blockage condition in the fluid flow path; and responsive to the counter no longer satisfying the first threshold, stop providing the first indication of the occurrence of the leak condition in the fluid flow path or the blockage condition in the fluid flow path.

2. The apparatus of claim 1, wherein the controller is further configured to:

responsive to the counter satisfying a second threshold subsequent to the counter satisfying the first threshold, provide a second indication of the occurrence of the leak condition in the fluid flow path or the blockage condition in the fluid flow path, the second indication being different from the first indication.

3. The apparatus of claim 2, wherein the first indication comprises an alert and the second indication comprises stopping provision of negative pressure to the wound by the negative pressure source.

4. The apparatus of claim 3, wherein the second threshold exceeds the first threshold.

5. The apparatus of claim 3, wherein the alert comprises a visual alert.

6. The apparatus of claim 1, wherein the controller is configured to monitor for the occurrence of the leak condition in the fluid flow path or the blockage condition in the fluid flow path during the time period based on comparing a level of activity of the negative pressure source over the time period to a leak activity threshold or a blockage activity threshold.

7. The apparatus of claim 6, wherein the level of activity of the negative pressure source comprises a duty cycle of the negative pressure source.

8. The apparatus of claim 1, wherein the controller is further configured to:

responsive to a determination that the negative pressure source is directly fluidically connected to the wound dressing, operate the negative pressure source in a first mode to provide negative pressure to the wound; and responsive to a determination that the negative pressure source is fluidically connected to the wound dressing via a canister positioned in the fluid flow path, operate the negative pressure source in a second mode to provide negative pressure to the wound, the second mode being different from the first mode.

9. The apparatus of claim 8, wherein the controller is further configured to set the first threshold based on operating the negative pressure source in the first mode or operating the negative pressure source in the second mode.

10. A kit comprising the apparatus of claim 1 and the wound dressing.

11. A method of operating a negative pressure wound therapy apparatus, the method comprising:

monitoring for an occurrence of a leak condition in a fluid flow path connecting the apparatus to a wound or a blockage condition in the fluid flow path during a time period of a plurality of time periods during which negative pressure is being provided to the wound;

at a first time, incrementing a counter responsive to detecting the occurrence of the leak condition or the blockage condition during the time period;

at a second time, responsive to not detecting the occurrence of the leak condition or the blockage condition during the time period:

at a third time, decrementing the counter to a value that is greater than zero if the counter has a value greater than one, and at a fourth time, decrementing the counter to a value of zero if the counter has a value of one;

at a fifth time, responsive to the counter satisfying a first threshold, providing a first indication of the occurrence of the leak condition or the blockage condition; and at a sixth time, responsive to the counter no longer satisfying the first threshold, stopping provision of the first indication of the occurrence of the leak condition or the blockage condition, wherein the method is performed under control of a controller of the apparatus.

12. The method of claim 11, further comprising:

at a seventh time, responsive to the counter satisfying a second threshold subsequent to the counter satisfying the first threshold, providing a second indication of the occurrence of the leak condition or the blockage condition, the second indication being different from the first indication.

13. The method of claim 12, wherein the first indication comprises an alert and the second indication comprises stopping provision of negative pressure to the wound.

14. The method of claim 13, wherein the second threshold exceeds the first threshold.

15. The method of claim 13, wherein the alert comprises a visual alert.

16. The method of claim 11, wherein monitoring for the occurrence of the leak condition or the blockage condition during the time period comprises comparing a level of activity of a negative pressure source of the apparatus over the time period to a leak activity threshold or a blockage activity threshold.

17. The method of claim 16, wherein the level of activity of the negative pressure source comprises a duty cycle of the negative pressure source.

18. The method of claim 11, further comprising:

at a seventh time, responsive to determining that a negative pressure source of the apparatus is directly fluidically connected to a wound dressing covering the wound, operating in a first mode to provide negative pressure to the wound; and at an eight time, responsive to determining that the negative pressure source is fluidically connected to the wound dressing via a canister positioned in the fluid flow path, operating in a second mode to provide negative pressure to the wound, the second mode being different from the first mode.

19. The method of claim 18, further comprising setting the first threshold based on operating in the first mode or operating in the second mode.

*     *     *     *     *